US006653125B2

(12) United States Patent
Donnelly et al.

(10) Patent No.: US 6,653,125 B2
(45) **Date of Patent: *Nov. 25, 2003**

(54) SYNTHETIC HEPATITIS C GENES

(75) Inventors: John J. Donnelly, Moraga, CA (US); Margaret A. Liu, Lafayette, CA (US); John W. Shiver, Doylestown, PA (US); Tong-Ming Fu, Lansdale, PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,949

(22) Filed: Feb. 17, 2000

(65) Prior Publication Data

US 2003/0053987 A1 Mar. 20, 2003

Related U.S. Application Data

(60) Provisional application No. 60/020,494, filed on Jun. 11, 1996, and provisional application No. 60/033,534, filed on Dec. 20, 1996.

(30) Foreign Application Priority Data

Jul. 12, 1996 (GB) ............................................ 9614731

(51) Int. Cl.[7] ............................................ C12N 15/79
(52) U.S. Cl. ................................. 435/320.1; 536/23.72
(58) Field of Search ......................... 514/44; 424/189.1, 424/228.1; 435/320.1; 536/23.72

(56) References Cited

U.S. PATENT DOCUMENTS

| | | | | |
|---|---|---|---|---|
| 5,514,539 A | | 5/1996 | Bukh et al. | 435/5 |
| 5,610,009 A | * | 3/1997 | Watanabe et al. | 435/5 |
| 5,786,464 A | | 7/1998 | Seed | |
| 6,235,888 B1 | * | 5/2001 | Pachuk et al. | 536/23.72 |

FOREIGN PATENT DOCUMENTS

| | | | |
|---|---|---|---|
| JP | 050696562 A | * | 3/1993 |
| WO | WO 90/11092 | | 10/1990 |
| WO | WO 93/17706 | | 9/1993 |
| WO | WO 95/33835 | | 12/1995 |
| WO | WO 96/10997 | | 4/1996 |

OTHER PUBLICATIONS

Farci et al. Science 258:135–140, Oct. 1992.*

Ray R., pp. 53–58, in Genetic Vaccines and Immunotherapeutic Strategies, Thibeault C.A. ed., International Business Communications, Southborough, MA, 1997.*

Tokushige et al. Hepatology 22 (4 Part 2):p220A., 1995.*

Chen et al. Vaccine Research 4/3:135–144, 1995.*

Lagging et al., Journal of Virology, 69(9):5859–5863, Sep. 1995.*

Selby, et al., "Expression, identification and subcellular localization of the proteins encoded by the hepatitis C viral genome", J. of Gen. Virol., vol. 74, pp. 1103–1113, 1993.

Bukh, et al., "Sequence analysis of the core gene of 14 hepatitis C virus genotypes", Proc. Natl. Acad. Sci. USA, vol. 91, pp. 8239–8243, Aug. 1994.

Lathe, "Synthetic Oligonucleotide Probes Deduced from Amino Acid Sequence Data". J.Mol. Biol., vol. 183, pp. 1–12, 1985.

Grantham, et al., "Codon catalog usage is a genome strategy modulated for gene expressivity", Nucleic Acid Res., vol. 9, No. 1, pp. R43–R74, 1981.

Ide, et al., Characterization of the nuclear localization signal and subcellular distribution of hepatitis C virus . . . , Gene, vol. 182, pp. 203–211, 1996.

Ulmer, et al., "Heterologous Protection Against Influenza by Injection of DNA Encoding a Viral Protein", Science, vol. 259, Mar. 19, 1993, pp. 1745–1749.

Zhu, et al., "Systemic Gene Expression After Intravenous DNA Delivery into Adult Mice", Science, vol. 261, Jul. 9, 1993, pp. 209–211.

Benvenisty, et al., "Direct introduction of genes into rats and expression of the genes", Proc. Natl. Acad. Sci., vol. 83, pp. 9551–9555, Dec. 1986.

Pachuk, C. et al. "HCV–Core DNA Vaccine, Constructs Induce an Anit–HCV Core Immune Response",1995 Vaccines, pp. 123–127.

Fu, T. et al. "Induction and Persistence of a Cytotoxic T Lymphocyte (CTL) Response against a Herpes Simplex Virus–Specific CTL Epitope Expressed in a Cellular Protein" Virology 222, 269–274, 1996.

* cited by examiner

*Primary Examiner*—Donna C. Wortman
(74) *Attorney, Agent, or Firm*—Sheldon O. Heber; Jack L. Tribble

(57) ABSTRACT

The present invention relates to polynucleotides comprising a DNA sequence encoding an HCV protein and fragments thereof that contain codons optimized for expression in a vertebrate host. Uses of the polynucleotides include eliciting an immune response specifically recognizing HCV.

3 Claims, 22 Drawing Sheets

| | 10 | 20 | 30 | 40 | 50 | 60 | 70 | 80 | |
|---|---|---|---|---|---|---|---|---|---|
| 1 | GATATTGGCT | ATTGGCCATT | GCATACGTTG | TATCCATATC | ATAATATGTA | CATTTATATT | GGCTCATGTC | CAACATTACC | 80 |
| 81 | GCCATGTTGA | CATTGATTAT | TGACTAGTTA | TTAATAGTAA | TCAATTACGG | GGTCATTAGT | TCATAGCCCA | TATATGGAGT | 160 |
| 161 | TCCGCGTTAC | ATAACTTACG | GTAAATGGCC | CGCCTGGCTG | ACCGCCCAAC | GACCCCCGCC | CATTGACGTC | AATAATGACG | 240 |
| 241 | TATGTTCCCA | TAGTAACGCC | AATAGGGACT | TTCCATTGAC | GTCAATGGGT | GGAGTATTTA | CGGTAAACTG | CCCACTTGGC | 320 |
| 321 | AGTACATCAA | GTGTATCATA | TGCCAAGTAC | GCCCCCTATT | GACGTCAATG | ACGGTAAATG | GCCCGCCTGG | CATTATGCCC | 400 |
| 401 | AGTACATGAC | CTTATGGGAC | TTTCCTACTT | GGCAGTACAT | CTACGTATTA | GTCATCGCTA | TTACCATGGT | GATGCGGTTT | 480 |
| 481 | TGGCAGTACA | TCAATGGGCG | TGGATAGCGG | TTTGACTCAC | GGGGATTTCC | AAGTCTCCAC | CCCATTGACG | TCAATGGGAG | 560 |
| 561 | TTTGTTTTGG | CACCAAAATC | AACGGGACTT | TCCAAAATGT | CGTAACAACT | CCGCCCCATT | GACGCAAATG | GGCGGTAGGC | 640 |
| 641 | GTGTACGGTG | GGAGGTCTAT | ATAAGCAGAG | CTCGTTTAGT | GAACCGTCAG | ATCGCCTGGA | GACGCCATCC | ACGCTGTTTT | 720 |
| 721 | GACCTCCATA | GAAGACACCG | GGACCGATCC | AGCCTCCGCG | GCCGGGAACG | GTGCATTGGA | ACGCGGATTC | CCCGTGCCAA | 800 |
| 801 | GAGTGACGTA | AGTACCGCCT | ATAGAGTCTA | TAGGCCCACC | CCCTTGGCTT | CTTATGCATG | CTATACTGTT | TTTGGCTTGG | 880 |
| 881 | GGTCTATACA | CCCCCGCTTC | CTCATGTTAT | AGGTGATGGT | ATAGCTTAGC | CTATAGGTGT | GGGTTATTGA | CCATTATTGA | 960 |
| 961 | CCACTCCCCT | ATTGGTGACG | ATACTTTCCA | TTACTAATCC | ATAACATGGC | TCTTTGCCAC | AACTCTCTTT | ATTGGCTATA | 1040 |
| 1041 | TGCCAATACA | CTGTCCTTCA | GAGACTGACA | CGGACTCTGT | ATTTTTACAG | GATGGGGTCT | CATTTATTAT | TTACAAATTC | 1120 |
| 1121 | ACATATACAA | CACCACCGTC | CCCAGTGCCC | GCAGTTTTTA | TTAAACATAA | CGTGGGATCT | CCACGCGAAT | CTCGGGTACG | 1200 |
| 1201 | TGTTCCGGAC | ATGGGCTCTT | CTCCGGTAGC | GGCGGAGCTT | CTACATCCGA | GCCCTGCTCC | CATGCCTCCA | GCGACTCATG | 1280 |
| 1281 | GTCGCTCGGC | AGCTCCTTGC | TCCTAACAGT | GGAGGCCAGA | CTTAGGCACA | GCACGATGCC | CACCACCACC | AGTGTGCCGC | 1360 |
| 1361 | ACAAGGCCGT | GGCGGTAGGG | TATGTGTCTG | AAAATGAGCT | CGGGGAGCGG | GCTTGCACCG | CTGACGCATT | TGGAAGACTT | 1440 |
| 1441 | AAGGCAGCGG | CAGAAGAAGA | TGCAGGCAGC | TGAGTTGTTG | TGTTCTGATA | AGAGTCAGAG | GTAACTCCCG | TTGCGGTGCT | 1520 |
| 1521 | GTTAACGGTG | GAGGGCAGTG | TAGTCTGAGC | AGTACTCGTT | GCTGCCGCGC | GCGCCACCAG | ACATAATAGC | TGACAGACTA | 1600 |
| 1601 | ACAGACTGTT | CCTTTCCATG | GGTCTTTTCT | GCAGTCACCG | TCCTTAGATC | TAGGTACCAG | ATATCAGAAT | TCAGTCGACA | 1680 |
| 1680 | GCGGCCGCGA | TCTGCTGTGC | CTTCTAGTTG | CCAGCCATCT | GTTGTTTGCC | CCTCCCCCGT | GCCTTCCTTG | ACCCTGGAAG | 1760 |
| 1761 | GTGCCACTCC | CAGTGTCCTT | TCCTAATAAA | ATGAGGAAAT | TGCATCGCAT | TGTCTGAGTA | GGTGTCATTC | TATTCTGGGG | 1840 |
| 1841 | GCTGGGGTGG | GGCAGCACAG | CAAGGGGGAG | GATTGGGAAG | ACAATAGCAG | GCATGCTGGG | GATGCGGTGG | GCTCTATGGG | 1920 |
| 1921 | TACGGCCGCA | GCGGCCTTAA | TTAAGGCCGC | AGCGGCCGTA | CCCAGGTGCT | GAAGAATTGA | CCCGGTTCCT | CGACCCGTAA | 2000 |

FIG. 1A

```
2001  AAAGGCCGCG TTGCTGGCGT TTTTCCATAG GCTCCGCCCC CCTGACGAGC ATCACAAAAA TCGACGCTCA AGTCAGAGGT 2080
2081  GGCGAAACCC GACAGGACTA TAAAGATACC AGGCGTTTCC CCCTGGAAGC TCCCTCGTGC GCTCTCCTGT TCCGACCCTG 2160
2161  CCGCTTACCG GATACCTGTC CGCCTTTCTC CCTTCGGGAA GCGTGGCGCT TTCTCAATGC TCACGCTGTA GGTATCTCAG 2240
2241  TTCGGTGTAG GTCGTTCGCT CCAAGCTGGG CTGTGTGCAC GAACCCCCCG TTCAGCCCGA CCGCTGCGCC TTATCCGGTA 2320
2321  ACTATCGTCT TGAGTCCAAC CCGGTAAGAC ACGACTTATC GCCACTGGCA GCAGCCACTG GTAACAGGAT TAGCAGAGCG 2400
2401  AGGTATGTAG GCGGTGCTAC AGAGTTCTTG AAGTGGTGGC CTAACTACGG CTACACTAGA AGGACAGTAT TTGGTATCTG 2480
2481  CGCTCTGCTG AAGCCAGTTA CCTTCGGAAA AAGAGTTGGT AGCTCTTGAT CCGGCAAACA AACCACCGCT GGTAGCGGTG 2560
2561  GTTTTTTTGT TTGCAAGCAG CAGATTACGC GCAGAAAAAA AGGATCTCAA GAAGATCCTT TGATCTTTTC TACGTGATCC 2640
2641  CGTAATGCTC TGCCAGTGTT ACAACCAATT AACCAATTCT GATTAGAAAA ACTCATCGAG CATCAAATGA AACTGCAATT 2720
2721  TATTCATATC AGGATTATCA ATACCATATT TTTGAAAAAG CCGTTTCTGT AATGAAGGAG AAAACTCACC GAGGCAGTTC 2800
2801  CATAGGATGG CAAGATCCTG GTATCGGTCT GCGATTCCGA CTCGTCCAAC ATCAATACAA CCTATTAATT TCCCCTCGTC 2880
2881  AAAAATAAGG TTATCAAGTG AGAAATCACC ATGAGTGACG ACTGAATCCG GTGAGAATGG CAAAAGCTTA TGCATTTCTT 2860
2961  TCCAGACTTG TTCAACAGGC CAGCCATTAC GCTCGTCATC AAAATCACTC GCATCAACCA AACCGTTATT CATTCGTGAT 3040
3041  TGCGCCTGAG CGAGACGAAA TACGCGATCG CTGTTAAAAG GACAATTACA AACAGGAATC GAATGCAACC GGCGCAGGAA 3120
3121  CACTGCCAGC GCATCAACAA TATTTTCACC TGAATCAGGA TATTCTTCTA ATACCTGGAA TGCTGTTTTC CCGGGGATCG 3200
3201  CAGTGGTGAG TAACCATGCA TCATCAGGAG TACGGATAAA ATGCTTGATG GTCGGAAGAG GCATAAATTC CGTCAGCCAG 3280
3281  TTTAGTCTGA CCATCTCATC TGTAACATCA TTGGCAACGC TACCTTTGCC ATGTTTCAGA AACAACTCTG GCGCATCGGG 3360
3361  CTTCCCATAC AATCGATAGA TTGTCGCACC TGATTGCCCG ACATTATCGC GAGCCCATTT ATACCCATAT AAATCAGCAT 3440
3441  CCATGTTGGA ATTTAATCGC GGCCTCGAGC AAGACGTTTC CCGTTGAATA TGGCTCATAA CACCCCTTGT ATTACTGTTT 3520
3521  ATGTAAGCAG ACAGTTTTAT TGTTCATGAT GATATATTTT TATCTTGTGC AATGTAACAT CAGAGATTTT GAGACACAAC 3600
3601  GTGGCTTTCC                                                                        3610
          |  10      |  20      |  30      |  40      |  50      |  60      |  70      |  80
```

FIG.1B

```
1/1                                     31/11
ATG AGC ACc AAc CCc AAg CCc CAg AGg AAg ACC AAg aGg AAC ACC AAC aGg aGg CCcCAG
Met ser thr asn pro lys pro gln arg lys thr lys arg asn thr asn arg arg pro gln
61/21                                   91/31
GAt GTg AAG TTC CCt GGg GGa GGc CAG ATt GTg GGa GGg GTc TAC cTG cTG CCc aGg AGG
asp val lys phe pro gly gly gly gln ile val gly gly val tyr leu leu pro arg arg
121/41                                  151/51
GGC CCC AGG cTG GGg GTG aGg GCt ACc aGG AAG ACc TCt GAG aGG TCc CAg CCC aGg GGC
gly pro arg leu gly val arg ala thr arg lys thr ser glu arg ser gln pro arg gly
181/61                                  211/71
AGG aGg CAG CCc ATC CCC AAG GCc aGg aGG CCt GAG GGC cGc TCC TGG GCc CAG CCt GGc
arg arg gln pro ile pro lys ala arg arg pro glu gly arg ser trp ala gln pro gly
241/81                                  271/81
TAC CCc TGG CCC CTg TAT GGC AAT GAa GGC TTt GGc TGG GCt GGc TGG CTG CTG TCC CCC
try pro trp pro leu tyr gly asn glu gly phe gly trp ala gly trp leu leu ser pro
301/101                                 331/111
aGg GGC TCc aGG CCc tcc TGG GGC CCC ACa GAC CCC aGG aGg aGG TCc aGg AAc cTG GGc
arg gly ser arg pro ser trp gly pro thr asp pro arg arg arg ser arg asn leu gly
361/121                                 391/131
AAg GTg ATt GAc ACC CTg ACc TGt GGC TTt GCt GAC CTg ATG GGc TAC ATC CCc CTg GTg
lys val ile asp thr leu thr cys gly phe ala asp leu met gly tyr ile pro leu val
421/141                                 451/151
GGg GCt CCt GTg GGa GGg GTg GCt AGG GCt CTG GCt CAT GGg GTg AGG GTg CTG GAG GAt
gly ala pro val gly gly val ala arg ala leu ala his gly val arg val leu glu asp
481/161                                 511/171
GGG GTG AAC TAT GCt ACt GGc AAc cTG CCt GGc TGC TCc TTC TCc ATC TTC CTg CTG GCc
gly val asn tyr ala thr gly asn leu pro gly cys ser phe ser ile phe leu leu ala
541/181                                 571/191
CTG CTc TCC TGC CTG ACa GTg CCt GCT TCT GCc
leu leu ser cys leu thr val pro ala ser ala
```

FIG. 5

```
1/1                                     31/11
ATG AGC ACG AAT CCT AAA CCT CAA AGA AAA ACC AAA CGT AAC ACC AAC CGC CGC CCa cAG
Met ser thr asn pro lys pro gln arg lys thr lys arg asn thr asn arg arg pro gln
61/21                                   91/31
GAc GTc AAg TTC CCg GGC GGt GGt CAG ATC GTT GGt GGA GTT TAC TTC TTG CCG CGC AGG
asp val lys phe pro gly gly gly gln ile val gly gly val tyr leu leu pro arg arg
121/41                                  151/51
GGC CCC AGG TTG GGT GTG CGC GCG ACT aGG AAG ACT TCc GAG CGG TCG CAA CCT CGT GGa
gly pro arg leu gly val arg ala thr arg lys thr ser glu arg ser gln pro arg gly
181/61                                  211/71
AGG CGa CAG CCT ATC CCC AAG GCt CGc CGG cCC GAG GGc AGG TCC TGG GCT CAG CCC GGG
arg arg gln pro ile pro lys ala arg arg pro glu gly arg ser trp ala gln pro gly
241/81                                  271/91
TAC CCt TGG CCc CTc TAt GGc AAT GAg GGC Ttc GGG TGG GCA GGa TGG CTC CTG TCC CCC
tyr pro trp pro leu tyr gly asn glu gly phe gly trp ala gly trp leu leu ser pro
301/101                                 331/111
CGC GGC TCT CGg CCt agT TGG GGC CCc AcT GAc CCC CGG CGt AGG TCG CGC AAT TTG GGT
arg gly ser arg pro ser trp gly pro thr asp pro arg arg arg ser arg asn leu gly
361/121                                 391/131
AAG GTC ATC GAT ACC CTC ACG TGC GGC TTC GCC GAC CTC ATG GGg TAC ATC CCG CTC GTc
lys val ile asp thr leu thr cys gly phe ala asp leu met gly tyr ile pro leu val
421/141                                 451/151
GGC GCC CCc GTA GGg GGC GTC GCC AGg GCC CTG GCG CAT GGC GTC AGG GtT cTG GAG GAC
gly ala pro val gly gly val ala arg ala leu ala his gly val arg val leu glu asp
481/161                                 511/171
GGG gtg AAC TAT GCA ACA GGG AAt tTg cCc GGT TGC TCT TTC TCT ATC TTC CTC cTG GCt
glu val asn tyr ala thr gly asn leu pro gly cys ser phe ser ile phe leu leu ala
541/181                                 571/191
CTg CTg TCc TGC CTG ACC GTC CCA GCt TCT GCT
leu leu ser cys leu thr val pro ala ser ala
```

FIG. 7

TABLE 3
CODON UTILIZATION IN HUMAN PROTEIN-CODING SEQUENCES

| a | b | c | d | e | f |
|---|---|---|---|---|---|
| F | UUU | 68 | 0.35 | 193 | 4.5 |
| | UUC | 125 | 0.65 | | |
| L | UUA | 20 | 0.05 | 445 | 10.4 |
| | UUG | 42 | 0.09 | | |
| | CUU | 50 | 0.11 | | |
| | CUC | 99 | 0.22 | | |
| | CUA | 30 | 0.07 | | |
| | CUG | 204 | 0.46 | | |
| I | AUU | 28 | 0.23 | 123 | 2.9 |
| | AUC | 79 | 0.64 | | |
| | AUA | 16 | 0.13 | | |
| M | AUG | 77 | 1.00 | 77 | 1.8 |
| V | GUU | 35 | 0.13 | 266 | 6.2 |
| | GUC | 72 | 0.27 | | |
| | GUA | 25 | 0.09 | | |
| | GUG | 134 | 0.50 | | |
| S | UCU | 59 | 0.17 | 349 | 8.1 |
| | UCC | 91 | 0.26 | | |
| | UCA | 37 | 0.11 | | |
| | UCG | 25 | 0.07 | | |
| | AGU | 37 | 0.11 | | |
| | AGC | 100 | 0.29 | | |
| P | CCU | 51 | 0.24 | 212 | 4.9 |
| | CCC | 86 | 0.41 | | |
| | CCA | 51 | 0.24 | | |
| | CCG | 24 | 0.11 | | |
| T | ACU | 47 | 0.20 | 238 | 5.6 |
| | ACC | 113 | 0.47 | | |
| | ACA | 50 | 0.21 | | |
| | ACG | 28 | 0.12 | | |
| A | GCU | 91 | 0.31 | 298 | 7.0 |
| | GCC | 119 | 0.40 | | |
| | GCA | 51 | 0.17 | | |
| | GCG | 37 | 0.12 | | |

| a | b | c | d | e | f |
|---|---|---|---|---|---|
| Y | UAU | 72 | 0.47 | 153 | 3.6 |
| | UAC | 81 | 0.53 | | |
| H | CAU | 44 | 0.42 | 105 | 2.5 |
| | CAC | 61 | 0.58 | | |
| Q | CAA | 50 | 0.26 | 192 | 4.5 |
| | CAG | 142 | 0.74 | | |
| N | AAU | 51 | 0.34 | 148 | 3.5 |
| | AAC | 97 | 0.66 | | |
| K | AAA | 137 | 0.45 | 303 | 7.0 |
| | AAG | 166 | 0.55 | | |
| D | GAU | 79 | 0.38 | 209 | 4.9 |
| | GAC | 130 | 0.62 | | |
| E | GAA | 125 | 0.40 | 311 | 7.3 |
| | GAG | 186 | 0.60 | | |
| C | UGU | 44 | 0.30 | 147 | 3.4 |
| | UGC | 103 | 0.70 | | |
| W | UGG | 56 | 1.00 | 56 | 1.3 |
| R | CGV | 19 | 0.09 | 215 | 5.0 |
| | CGC | 40 | 0.19 | | |
| | CGA | 22 | 0.10 | | |
| | CGG | 33 | 0.15 | | |
| | AGA | 51 | 0.24 | | |
| | AGG | 50 | 0.23 | | |
| G | GGU | 36 | 0.15 | 245 | 5.7 |
| | GGC | 108 | 0.44 | | |
| | GGA | 42 | 0.17 | | |
| | GGG | 59 | 0.24 | | |

TOTAL 4285 RESIDUES EXCLUDING
N-TERMINAL METHIONINE RESIDUES

FIG.8

```
1/1                                     31/11
atg TAT GAg GTG aGg AAt GTc TCt GGc GTc TAC CAT GTg ACc AAt GAC TGC TCC AAC TCc
M   Y   E   V   R   N   V   S   G   V   Y   H   V   T   N   D   C   S   N   S
61/21                                   91/31
tGc ATT GTc TAT GAG GCt GCt GAC ATG ATc ATG CAc ACC CCt GGc TGt GTg CCa TGt GTg
C   I   V   Y   E   A   A   D   M   I   M   H   T   P   G   C   V   P   C   V
121/41                                  151/71
aGG GAG GGc AAc TCC TCC aGg TGC TGG GTg GCc CTg ACc CCC ACc CTg GCt GCC AGG AAC
R   E   G   N   S   S   R   C   W   V   A   L   T   P   T   L   A   A   R   N
181/61                                  211/71
tcC tcC ATC CCC ACc ACc ACc ATc aGg aGg CAT GTg GAc cTG CTg GTg GGc GCt GCT GCc
S   S   I   P   T   T   T   I   R   R   H   V   D   L   L   V   G   A   A   A
241/81                                  271/91
CTg TGC TCt GCc ATG TAt GTG GGc GAc CTg TGT GGc TCT GTc TTC CTg GTg TCC CAg gTG
L   C   S   A   M   Y   V   G   D   L   C   G   S   V   F   L   V   S   Q   L
301/101                                 331/111
TTC ACC TTC TCc CCc aGg aGG TAT GAG ACt GTg CAG GAC TGC AAc TGC TCc CTg TAc CCt
F   T   F   S   P   R   R   Y   E   T   V   Q   D   C   N   C   S   L   Y   P
361/121                                 391/131
GGC CAt GTc TCt GGc CAC aGg ATG GCc TGG GAc ATG ATG ATG AAC TGG TCc CCc ACc ACt
G   H   V   S   G   H   R   M   A   W   D   M   M   M   N   W   S   P   T   T
421/141                                 451/151
GCC cTg GTG GTc TCc CAG cTg CTg aGG ATt CCc CAg GCt GTg GTG GAC ATG GTG TGT GGg
A   L   V   V   S   Q   L   L   R   I   P   Q   A   V   V   D   M   V   V   G
481/161                                 511/171
GCC CAC TGG GGc GTg CTG GCt GGC CTg GCC TAC TAc TCC ATG GTG GGc AAC TGG GCc AAG
A   H   W   G   V   L   A   G   L   A   Y   Y   S   M   V   G   N   W   A   K
541/181                                 571/191
GTg cTG ATT GTG ATG CTg CTg TTT GCt GGC GTg GAt GGc taa
V   L   I   V   M   L   L   F   A   G   V   D   G   *
```

FIG. 9

```
1/1                                         31/11
atg ACc ACC TAt GTc TCt GTG GGc CAT GCc tcC CAG ACC ACC aGG aGg GTg GCc TCC TTC
M   T   T   Y   V   S   V   G   H   A   S   Q   T   T   R   R   V   A   S   F
61/21                                       91/31
TTC tcc CCT GGC TCt GCc CAG AAg ATC CAg CTg GTg AAC ACC AAt GGC tcc TGG CAC ATC
F   S   P   G   S   A   Q   K   I   Q   L   V   N   T   N   G   S   W   H   I
121/41                                      151/51
AAC AGG ACT GCC CTG AAt TGC AAt GAG TCC ATC AAC ATC GGc TTC TTT GCt GCc CTG TTC
N   R   T   A   L   N   C   N   E   S   I   N   T   G   F   F   A   A   L   F
181/61                                      211/71
TAt GTg AAG AAG TTC AAC TCc TCT GGc TGC TCt GAG aGg ATG GCc tct TGc aGg CCC ATT
Y   V   K   K   F   N   S   S   G   C   S   E   R   M   A   S   C   R   P   I
241/81                                      271/91
GAC AGG TTt GCc CAg GGc TGG GGc CCC ATC ACC CAT GCT GAG TCc aGg tcC TCt GAC CAg
D   R   F   A   Q   G   W   G   P   I   T   H   A   E   S   R   S   S   D   Q
301/101                                     331/111
AGG CCa TAC TGC TGG CAC TAt GCc CCc CAg CCa TGT GGc ATt GTG CCt GCc cTG CAt GTc
R   P   Y   C   W   H   Y   A   P   Q   P   C   G   I   V   P   A   L   H   V
361/121                                     391/131
TGt GGc CCt GTc TAc TGc TTC ACC CCa tcC CCT GTg GTg GTG GGc ACg ACt GAC aGg TTt
C   G   P   V   Y   C   F   T   P   S   P   V   V   V   G   T   T   D   R   F
421/141                                     451/151
GGC GTg CCC ACc TAc AAC TGG GGc GAC AAT GAG ACt GAt GTG CTg CTg CTG AAC AAC ACc
G   V   P   T   Y   N   W   G   D   N   E   T   D   V   L   L   L   N   N   T
481/161                                     511/171
aGG CCc CCc CAg GGc AAC TGG TTt GGC TGc ACc TGG ATG AAC tcC ACt GGc TTC ACC AAG
R   P   P   Q   G   N   W   F   G   C   T   W   M   N   S   T   G   F   T   K
```

FIG.10A

```
541/181                                 571/191
ACc TGt GGc GGC CCC CCa TGc AAc ATt GGc GGc GCt GGC AAC AAC ACC cTG ACC TGC CCC
T   C   G   G   P   P   C   N   I   G   G   A   G   N   N   T   L   T   C   P
601/201                                 631/211
ACt GAc TGC TTC aGG AAG CAt CCt GAG GCC ACc TAC ACC AAG TGt GGC TCt GGc CCa TGG
T   D   C   F   R   K   H   P   E   A   T   Y   T   K   C   G   S   G   P   W
661/221                                 691/231
cTG ACc CCc AGG TGC ATG GTg GAC TAC CCa TAC AGg CTg TGG CAC TAC CCa TGC ACc TTC
L   T   P   R   C   M   V   D   Y   P   Y   R   L   W   H   Y   P   C   T   F
721/241                                 751/251
AAC TTc ACC ATC TTc AAG ATC AGG ATG TAT GTG GGc GGc GTG GAG CAC AGG CTg AAt GCt
N   F   T   I   F   K   I   R   M   Y   V   G   G   V   E   H   R   L   N   A
781/261                                 811/271
GCc TGC AAC TGG ACc aGg GGc GAG aGg TGc AAC ATt GAG GAC AGG GAc AGG TCt GAG CTg
A   C   N   W   T   R   G   E   R   C   N   I   E   D   R   D   R   S   E   L
841/281                                 871/291
tcC CCc CTG CTg CTG TCc ACc ACt GAG TGG CAG ATc CTg CCa TGc TCC TTc ACC ACC CTg
S   P   L   L   L   S   T   T   E   W   Q   I   L   P   C   S   F   T   T   L
901/301                                 931/311
CCt GCc CTG TCC ACT GGc cTG ATC CAt CTg CAt CAG AAC ATt GTG GAt GTG CAg TAC CTG
P   A   L   S   T   G   L   I   H   L   H   Q   N   I   V   D   V   Q   Y   L
961/321                                 991/331
TAt GGc GTg GGc TCt GCt GTg GTc TCC ATT GTG ATC AAg TGG GAG TAt GTg CTG CTG CTg
Y   G   V   G   S   A   V   V   S   I   V   I   K   W   E   Y   V   L   L   L
1021/341
TTC CTg CTg CTG GCt GAt GCc taa
F   L   L   L   A   D   A   *
```

FIG.10B

```
1/1                                     31/11
atg TAT GAg GTG aGg AAt GTc TCt GGc GTc TAC CAT GTg ACc AAt GAC TGC TCC AAC TCc
M   Y   E   V   R   N   V   S   G   V   Y   H   V   T   N   D   C   S   N   S
61/21                                   91/31
tGc ATT GTc TAT GAG GCt GCt GAC ATG ATc ATG CAc ACC CCt GGc TGt GTg CCa TGt GTg
C   I   V   Y   E   A   A   D   M   I   M   H   T   P   G   C   V   P   C   V
121/41                                  151/51
aGG GAG GGc AAc TCC TCC aGg TGC TGG GTg GCc CTg ACc CCC ACc CTg GCt GCC AGG AAC
R   E   G   N   S   S   R   C   W   V   A   L   T   P   T   L   A   A   R   N
181/61                                  211/71
tcC tcC ATC CCC ACc ACc ACc ATc aGg aGg CAT GTg GAc cTG CTg GTg GGc GCt GCT GCc
S   S   I   P   T   T   T   I   R   R   H   V   D   L   L   V   G   A   A   A
241/81                                  271/91
CTg TGC TCt GCc ATG TAt GTG GGc GAc CTg TGT GGc TCT GTc TTC CTg GTg TCC CAg cTG
L   C   S   A   M   Y   V   G   D   L   C   G   S   V   F   L   V   S   Q   L
301/101                                 331/111
TTC ACC TTC TCc CCc aGg aGG TAT GAG ACt GTg CAG GAC TGC AAc TGC TCc CTg TAc CCt
F   T   F   S   P   R   R   Y   E   T   V   Q   D   C   N   C   S   L   Y   P
361/121                                 391/131
GGC CAt GTc TCt GGc CAC aGg ATG GCc TGG GAc ATG ATG ATG AAC TGG TCc CCc ACc ACt
G   H   V   S   G   H   R   M   A   W   D   M   M   M   N   W   S   P   T   T
421/141                                 451/151
GCC cTg GTG GTc TCc CAG cTg CTg aGG ATt CCc CAg GCt GTg GTG GAC ATG GTG GTG GGc
A   L   V   V   S   Q   L   L   R   I   P   Q   A   V   V   D   M   V   V   G
481/161                                 511/171
GCC CAC TGG GGc GTg CTG GCt GGC CTg GCC TAC TAc TCC ATG GTG GGc AAC TGG GCc AAG
A   H   W   G   V   L   A   G   L   A   Y   Y   S   M   V   G   N   W   A   K
```

FIG.11A

```
541/181                                 571/191
GTg cTG ATT GTG ATG CTg CTg TTT GCt GGC GTg GAt GGc ACc ACC TAt GTc TCt GTG GGc
V   L   I   V   M   L   L   F   A   G   V   D   G   T   T   Y   V   S   V   G
601/201                                 631/211
CAT GCc tcC CAG ACC ACC aGG aGg GTg GCc TCC TTC TTC tcc CCT GGC TCt GCc CAG AAg
H   A   S   Q   T   T   R   R   V   A   S   F   F   S   P   G   S   A   Q   K
661/221                                 691/231
ATC CAg CTg GTg AAC ACC AAt GGC tcc TGG CAC ATC AAC AGG ACT GCC CTG AAt TGC AAt
I   Q   L   V   N   T   N   G   S   W   H   I   N   R   T   A   L   N   C   N
721/241                                 751/251
GAG TCC ATC AAC ACT GGc TTC TTT GCt GCc CTG TTC TAt GTg AAG AAG TTC AAC TCc TCT
E   S   I   N   T   G   F   F   A   A   L   F   Y   V   K   K   F   N   S   S
781/261                                 811/271
GGc TGC TCt GAG aGg ATG GCc tct TGc aGg CCC ATT GAC AGG TTt GCc CAg GGc TGG GGc
G   C   S   E   R   M   A   S   C   R   P   I   D   R   F   A   Q   G   W   G
841/281                                 871/291
CCC ATC ACC CAT GCT GAG TCc aGg tcC TCt GAC CAg AGG CCa TAC TGC TGG CAC TAt GCc
P   I   T   H   A   E   S   R   S   S   D   Q   R   P   Y   C   W   H   Y   A
901/301                                 931/311
CCc CAg CCa TGT GGc ATt GTG CCt GCc cTG CAt GTc TGt GGc CCt GTc TAc TGc TTC ACC
P   Q   P   C   G   I   V   P   A   L   H   V   C   G   P   V   Y   C   F   T
961/321                                 991/331
CCa tcC CCT GTg GTg GTG GGc ACc ACt GAC aGg TTt GGC GTg CCC ACc TAc AAC TGG GGc
P   S   P   V   V   V   G   T   T   D   R   F   G   V   P   T   Y   N   W   G
1021/341                                1051/351
GAC AAT GAG ACt GAt GTG CTg CTg CTg AAC AAC ACc aGG CCc CCc CAg GGc AAC TGG TTe
D   N   E   T   D   V   L   L   L   N   N   T   R   P   P   Q   G   N   W   F
```

FIG.11B

```
1081/361                                1111/37
GGC TGc ACc TGG ATG AAC tcC ACt GGc TTC ACC AAG ACc TGt GGc GGC CCC CCa TGc AAc
G   C   T   W   M   N   S   T   G   F   T   K   T   C   G   G   P   P   C   N
1141/381                                1171/391
ATt GGc GGc GCt GGC AAC AAC ACC cTG ACC TGC CCC ACt GAc TGC TTC aGG AAG CAt CCt
I   G   G   A   G   N   N   T   L   T   C   P   T   D   C   F   R   K   H   P
1201/401                                1231/411
GAG GCC ACc TAC ACC AAG TGt GGC TCt GGc CCa TGG cTG ACc CCc AGG TGC ATG GTg GAC
E   A   T   Y   T   K   C   G   S   G   P   W   L   T   P   R   C   M   V   D
1261/421                                1291/431
TAC CCa TAC AGg CTg TGG CAC TAC CCa TGC ACc TTC AAC TTc ACC ATC TTc AAG ATC AGG
Y   P   Y   R   L   W   H   Y   P   C   T   F   N   F   T   I   F   K   I   R
1321/441                                1351/451
ATG TAT GTG GGc GGc GTG GAG CAC AGG CTg AAt GCt GCc TGC AAC TGG ACc aGg GGc GAG
M   Y   V   G   G   V   E   H   R   L   N   A   A   C   N   W   T   R   G   E
1381/461                                1411/471
aGg TGc AAC ATg GAG CAC AGG GAc AGG TCt GAG CTg tcC CCc CTG CTg CTG TCc ACc ACt
R   C   N   I   E   D   R   D   R   S   E   L   S   P   L   L   L   S   T   T
1441/481                                1471/491
GAG TGG CAG ATc CTg CCa TGc TCC TTc ACC ACC CTg CCt GCc CTG TCC ACT GGc cTG ATC
E   W   Q   I   L   P   C   S   F   T   T   L   P   A   L   S   T   G   L   I
1501/501                                1531/511
CAt CTg CAt CAG AAC ATt GTG GAt GTG CAg TAC CTG TAt GGc GTg GGc TCt GCt GTg GTc
H   L   H   Q   N   I   V   D   V   Q   Y   L   Y   G   V   G   S   A   V   V
1561/521                                1591/531
TCC ATT GTG ATC AAg TGG GAG TAt GTg CTG CTG CTg TTC CTg CTg CTG GCt GAt GCc taa
S   I   V   I   K   W   E   Y   V   L   L   L   F   L   L   L   A   D   A   *
```

FIG.11C

```
1/1                                      31/11
atg TCt GGc TCc TGG CTg AGG GAT GTc TGG GAC TGG ATc TGC ACt GTG cTG ACT GAC TCC
M   S   G   S   W   L   R   D   V   W   D   W   I   C   T   V   L   T   D   F
61/21                                    91/31
AAG ACC TGG CTg CAt TCC AAG CTg CTG CCc aGG CTG CCt GGc GAC CCa TTC TTC TCc TGc
K   T   W   L   H   S   K   L   L   P   R   L   P   G   D   P   F   F   S   C
121/41                                   151/51
CAg aGg GGc TAC AGG GGc GTc TGG aGG GGc GAT GGC GTg ATG CAg ACC ACC TGC CCa TGT
Q   R   G   Y   R   G   V   W   R   G   D   G   V   M   Q   T   T   C   P   C
181/61                                   211/71
GGc GCc CAG ATC ACt GGc CAT GTg AAg AAt GGc TCC ATG AGG ATt GTg GGc CCc AAg ACC
G   A   Q   I   T   G   H   V   K   N   G   S   M   R   I   V   G   P   K   T
241/81                                   271/91
TGc tcC AAC ACc TGG CAt GGc ACc TTC CCC ATC AAt GCc TAC ACC ACt GGc CCa TGC ACc
C   S   N   T   W   H   G   T   F   P   I   N   A   Y   T   T   G   P   C   T
301/101                                  331/111
CCa TCC CCt GCc CCc AAC TAc TCC AGG GCc CTG TGG aG GTG GCT GCT GAG GAG TAT GTG
P   S   P   A   P   N   Y   S   R   A   L   W   R   V   A   A   E   Y   V   V
361/121                                  391/131
GAg GTg ACc aGG GTG GGc GAc TTC CAC TAt GTG ACt GGC ATG ACC ACT GAC AAt GTg AAg
E   V   T   R   V   G   D   F   H   Y   V   T   G   M   T   T   D   N   V   K
421/141                                  451/151
TGC CCa TGC CAG GTg CCt GCC CCt GAg TTC TTC ACt GAg GTG GAT GGc GTG aGG cTG CAC
C   P   C   Q   V   P   A   P   E   F   F   T   E   V   D   G   V   R   L   H
481/161                                  511/171
AGG TAt GCc CCt GCc TGC AAg CCc CTg CTg aGG GAT GAG GTg ACc TTC CAG GTg GGc CTg
R   Y   A   P   A   C   K   P   L   L   R   D   E   V   T   F   Q   V   G   L
```

FIG.12A

```
541/181
AAC CAg TTC CCt GTg GGc TCC CAG CTg CCa TGT GAG CCt GAg CCt GAT GTg ACt GTG CTg
 N   Q   F   P   V   G   S   Q   L   P   C   E   P   E   P   D   V   T   V   L
                                          571/191
601/201
ACC TCC ATG CTg ACt GAg CCa TCC CAC ATc ACt GCt GAG ACt GCc AAG aGg AGG cTG GCC
 T   S   M   L   T   E   P   S   H   I   T   A   E   T   A   K   R   R   L   A
                                 631/211
661/221
AGg GGc TCc CCt CCa TCC cTG GCC tcC TCc CAG CTG TCT GCt CCa TCC cTG
 R   G   S   P   P   S   L   A   S   S   Q   L   S   A   P   S   L
                          691/231
721/241
AAG GCc ACc TGC ACc ACC aGg CAT GAC TCC CCt GAt GCt GAC CTg ATt GAG GCC AAC CTg
 K   A   T   C   T   T   R   H   D   S   P   D   A   D   L   I   E   A   N   L
                                 751/251
781/261
CTG TGG aGG CAG GAG ATG GGC GGc AAC ATC ACC aGG GTG GAG TCt GAG AAc AAG GTg GTg
 L   W   R   Q   E   M   G   G   N   I   T   R   V   E   S   E   N   K   V   V
                                          811/271
841/281
ATc CTg GAC TCc TTT GAg CCc CTg aGG GCt GAG GAG GAT GAG GAG GTc TCt GTG GCt
 I   L   D   S   F   E   P   L   R   A   E   E   D   E   E   V   S   V   A
                          871/291
901/301
GCt GAG ATC CTg aGG AAg tCC AGG AAG TTC CCC CCt GCc cTG CCC ATc TGG GCg aGg CCa
 A   E   I   L   R   K   S   R   K   F   P   P   A   L   P   I   W   A   R   P
                                 931/311
961/321
tCC TAC AAC CCa CCC CTG CTg GAG TCC TGG AAG GAC CCt GAC TAt GTg CCc CCt GTG GTg
 S   Y   N   P   P   L   L   E   S   W   K   D   P   D   Y   V   P   P   V   V
                                          991/331
1021/381
CAt GGc TGC CCc CTG CCc CCc ACC ATG GCc CCa CCc ATc CCc CCa aGG AGG AAG AGG
 H   G   C   P   L   P   P   T   M   A   P   P   I   P   P   R   R   K   R
```

FIG.12B

```
1081/361                                1111/371
ACt GTg GTg CTG ACt GAg TCC ACt GTc TCc TCT GCC cTG GCT GAG CTg GCC ACc AAG ACC
T   V   V   L   T   E   S   T   V   S   S   A   L   A   E   L   A   T   K   T
1141/381                                1171/391
TTC GGC tcC TCt GGc TCc TCt GCt GTg GAC tct GGC ACt GCc ACG GCC CCc CCT GAC CAG
F   G   S   S   G   S   S   A   V   D   S   G   T   A   T   A   P   P   D   Q
1201/401                                1231/411
CCa TCt GAT GAt GGc GAC AGg GGc TCt GAt GAT GAG TCc TAC TCC TCC ATG CCC CCC CTg
P   S   D   D   G   D   R   G   S   D   D   E   S   Y   S   S   M   P   P   L
1261/421                                1291/431
GAG GGc GAG CCt GGc GAC CCt GAc CTg tct GAt GGc TCc TGG TCc ACt GTc tct GAG GAG
E   G   E   P   G   D   P   D   L   S   D   G   S   W   S   T   V   S   E   E
1321/441
GCc tct GAG GAt GTg GCc TGC TGC TCc taa
A   S   E   D   V   A   C   C   S   *
```

FIG.12C

```
1/1                                     31/11
ATG TCc TAC ACc TGG ACt GGC GCC CTg ATC ACc CCa TGt GCt GCt GAG GAG tcC AAG CTG
M   S   Y   T   W   T   G   A   L   I   T   P   C   A   A   E   E   S   K   L
61/21                                   91/31
CCC ATC AAc CCc cTG tcC AAC TCc cTG CTG aGg CAt CAC AAC ATG GTc TAt GCC ACc ACc
P   I   N   P   L   S   N   S   L   L   R   H   H   N   M   V   Y   A   T   T
121/41                                  151/51
TCc aGg tct GCt GGC CTg aGG CAG AAg AAG GTg ACC TTT GAC AGg CTG CAt GTg CCt GAt
S   R   S   A   G   L   R   Q   K   K   V   T   F   D   R   L   H   V   P   C
181/61                                  211/71
GAC CAc TAC aGG GAt GTG CTg AAG GAG ATG AAG GCc AAG GCc TCC ACt GTg AAG GCg AAg
D   H   Y   R   D   V   L   K   E   M   K   A   K   A   S   T   V   K   A   K
241/81                                  271/91
CTg CTg TCT GTg GAg GAg GCC TGC AAG CTG ACc CCt CCc CAC TCt GCC AGg TCC AAg TTT
L   L   S   V   E   E   A   C   K   L   T   P   P   H   S   A   R   S   K   F
301/101                                 331/111
GGC TAT GGc GCc AAG GAt GTg aGG AAC CTg TCC tcC AAG GCt GTg AAC CAC ATC CAC TCt
G   Y   G   A   K   D   V   R   N   L   S   S   K   A   V   N   H   I   H   S
361/121                                 391/131
GTc TGG AAG GAC cTG CTG GAg GAC ACT GAg ACc CCc ATT GAC ACc ACC ATC ATG GCc AAg
V   W   K   D   L   L   E   D   T   E   T   P   I   D   T   T   I   M   A   K
421/141                                 451/151
AAT GAG GTc TTC TGT GTg CAg CCt GAG AAg GGc GGC aGg AAG CCt GCC aGg CTg ATt GTc
N   E   V   F   C   V   Q   P   E   K   G   G   R   K   P   A   R   L   I   V
481/161                                 511/171
TTC CCt GAg CTg GGc GTg aGg GTG TGt GAG AAg ATG GCC CTg TAt GAt GTG GTc TCC ACc
F   P   E   L   G   V   R   V   C   E   K   M   A   L   Y   D   V   V   S   T
```

FIG.13A

```
541/181                                 571/191
CTg CCc CAG GCt GTG ATG GGC TCC TCc TAt GGc TTC CAG TAC TCc CCT GGc CAG aGG GTg
L   P   Q   A   V   M   G   S   S   Y   G   F   Q   Y   S   P   G   Q   R   V
601/201                                 631/211
GAG TTC CTG GTG AAT GCC TGG AAg TCc AAG AAg AAC CCc ATG GGC TTt GCc TAc TGC ACC
E   F   L   V   N   A   W   K   S   K   K   N   P   M   G   F   A   Y   C   T
661/221                                 691/231
aGg TGc TTT GAC TCc ACt GTg ACT GAG tcT GAc ATC aGg GTg GAG GAG TCc ATc TAC CAg
R   C   F   D   S   T   V   T   E   S   D   I   R   V   E   E   S   I   Y   Q
721/241                                 751/251
TGc TGT GAC cTG GCt CCt GAG GCC AGg CAG GTg ATc AGG TCc CTg ACt GAG aGG CTg TAc
C   C   D   L   A   P   E   A   R   Q   V   I   R   S   L   T   E   R   L   Y
781/261                                 811/271
ATt GGc GGC CCC CTG ACc AAc TCc AAg GGc CAG AAC TGt GGc TAc aGg aGG TGC aGg GCC
I   G   G   P   L   T   N   S   K   G   Q   N   C   G   Y   R   R   C   R   A
841/281                                 871/291
tct GGc GTG CTG ACc ACT AAC TGt GGc AAc ACC CTg ACc TGc TAC cTG AAG GCC TCT GCt
S   G   V   L   T   T   N   C   G   N   T   L   T   C   Y   L   K   A   S   A
901/301                                 931/311
GCt TGc aGg GCT GCc AAG CTg CAt GAC TGC ACc ATG CTg GTc TGt GGc GAt GAC CTg GTg
A   C   R   A   A   K   L   H   D   C   T   M   L   V   C   G   D   D   L   V
961/321                                 991/331
GTg ATC TGT GAg tct GCt GGc ACC CAG GAG GAt GCt GCc tcC CTg aGg GTc TTC ACt GAG
V   I   C   E   S   A   G   T   Q   E   D   A   A   S   L   R   V   F   T   E
1021/341                                1051/351
GCc ATG ACc AGG TAC TCT GCC CCc CCt GGc GAC CCt CCC CAg CCt GAg TAt GAC cTG GAG
A   M   T   R   Y   S   A   P   P   G   D   P   P   Q   P   E   Y   D   L   E
```

FIG.13B

```
1081/361                                1111/371
cTg ATc ACc TCc TGC TCC TCC AAt GTc TCt GTg GCc CAt GAt GCc TCT GGC AAG aGG GTc
L   I   T   S   C   S   S   N   V   S   V   A   H   D   A   S   G   K   R   V
1141/381                                1171/391
TAC TAC CTg ACc aGg GAC CCC ACC ACC CCc CTg GCc AGG GCt GCc TGG GAg ACt GCc AGg
Y   Y   L   T   R   D   P   T   T   P   L   A   R   A   A   W   E   T   A   R
1201/401                                1231/411
CAC ACc CCt GTg AAC TCC TGG CTg GGC AAC ATC ATC ATG TAt GCc CCC ACC CTG TGG GCc
H   T   P   V   N   S   W   L   G   N   I   I   M   Y   A   P   T   L   W   A
1261/421                                1291/431
AGG ATG ATc CTG ATG ACC CAC TTC TTC TCC ATC CTg CTg GCc CAG GAG CAg CTg GAg AAg
R   M   I   L   M   T   H   F   F   S   I   L   L   A   Q   E   Q   L   E   K
1321/441                                1351/451
GCC CTG GGc TGc CAG ATt TAt GGc GCC ACc TAC TTC ATT GAg CCc CTg GAC CTg CCc CAG
A   L   G   C   Q   I   Y   G   A   T   Y   F   I   E   P   L   D   L   P   Q
1381/461                                1411/471
ATC ATc CAG aGg CTg CAt GGc CTg tct GCc TTc TCc CTg CAC tcc TAC TCc CCt GGc GAg
I   I   Q   R   L   H   G   L   S   A   F   S   L   H   S   Y   S   P   G   E
1441/481                                1471/491
ATC AAc AGG GTG GCc TCc TGC CTg AGG AAg CTg GGc GTg CCc CCC cTG aGg GTg TGG AGg
I   N   R   V   A   S   C   L   R   K   L   G   V   P   P   L   R   V   W   R
1501/501                                1531/511
GAc aGG GCC AGg tct GTg aGg GCc AAG CTg CTG TCC CAG GGc GGc AGG GCt GCC ACc TGT
H   R   A   R   S   V   R   A   K   L   L   S   Q   G   G   R   A   A   T   C
1561/521                                1591/531
GGC AAG TAC CTg TTC AAC TGG GCt GTG AGG ACC AAG CTg AAg CTg ACc CCc ATc CCt GCT
G   K   Y   L   F   N   W   A   V   R   T   K   L   K   L   T   P   I   P   A
```

FIG.13C

```
1621/541                                1651/551
GCc TCC CAG cTG GAC cTg TCt GGC TGG TTt GTg GCT GGc TAC tct GGc GGc GAC ATc TAc
A   S   Q   L   D   L   S   G   W   F   V   A   G   Y   S   G   G   D   I   Y
1681/561                                1711/571
CAC tcC CTG TCc aGg GCC aGg CCC aGg TGG TTC ATG TGG TGC CTg CTg CTg CTg TCT GTg
H   S   L   S   R   A   R   P   R   W   F   M   W   C   L   L   L   L   S   V
1741                                    1771/591
GGc GTg GGC ATC TAC CTG CTg CCC AAC aGG TGA
G   V   G   I   Y   L   L   P   N   R   *
```

FIG.13D

SYNTHETIC HEPATITIS C GENES

CROSS-REFERENCE TO RELATED APPLICATIONS

The present application is a 371 of PCT/US97/09884, filed Jun. 6, 1997, which claims benefit of U.S. provisional application 60/020,494 filed Jun. 11, 1996, now abandoned, and U.S. provisional application 60/033,534 filed Dec. 20, 1996, now abandoned.

STATEMENT REGARDING FEDERALLY-SPONSORED R&D

Not applicable.

REFERENCE TO MICROFICHE APPENDIX

Not applicable.

FIELD OF THE INVENTION

Not applicable.

BACKGROUND OF THE INVENTION

This invention relates to novel nucleic acid pharmaceutical products, specifically nucleic acid vaccine products. The nucleic acid vaccine products, when introduced directly into muscle cells, induce the production of immune responses which specifically recognize Hepatitis C virus (HCV).

Hepatitis C Virus

Non-A, Non-B hepatitis (NANBH) is a transmissible disease (or family of diseases) that is believed to be virally induced, and is distinguishable from other forms of virus-associated liver disease, such as those caused by hepatitis A virus (HAV), hepatitis B virus (HBV), delta hepatitis virus (HDV), cytomegalovirus (CMV) or Epstein-Barr virus (EBV). Epidemiologic evidence suggests that there may be three types of NANBH: the water-borne epidemic type; the blood or needle associated type; and the sporadically occurring (community acquired) type. However, the number of causative agents is unknown. Recently, a new viral species, hepatitis C virus (HCV) has been identified as the primary (if not only) cause of blood-associated NANBH (BB-NANBH). Hepatitis C appears to be the major form of transfusion-associated hepatitis in a number of countries, including the United States and Japan. There is also evidence implicating HCV in induction of hepatocellular carcinoma. Thus, a need exists for an effective method for preventing or treating HCV infection: currently, there is none.

The HCV may be distantly related to the flaviviridae. The Flavivirus family contains a large number of viruses which are small, enveloped pathogens of man. The morphology and composition of Flavivirus particles are known, and are discussed in M. A. Brinton, in "The Viruses: The Togaviridae And Flaviviridae" (Series eds. Fraenkel-Conrat and Wagner, vol. eds. Schlesinger and Schlesinger, Plenum Press, 1986), pp. 327–374. Generally, with respect to morphology, Flaviviruses contain a central nucleocapsid surrounded by a lipid bilayer. Virions are spherical and have a diameter of about 40–50 nm. Their cores are about 25–30 nm in diameter. Along the outer surface of the virion envelope are projections measuring about 5–10 nm in length with terminal knobs about 2 nm in diameter. Typical examples of the family include Yellow Fever virus, West Nile virus, and Dengue Fever virus. They possess positive-stranded RNA genomes (about 11,000 nucleotides) that are slightly larger than that of HCV and encode a polyprotein precursor of about 3500 amino acids. Individual viral proteins are cleaved from this precursor polypeptide.

The genome of HCV appears to be single-stranded RNA containing about 10,000 nucleotides. The genome is positive-stranded, and possesses a continuous translational open reading frame (ORF) that encodes a polyprotein of about 3,000 amino acids. In the ORF, the structural proteins appear to be encoded in approximately the first quarter of the N-terminal region, with the majority of the polyprotein attributed to non-structural proteins. When compared with all known viral sequences, small but significant co-linear homologies are observed with the nonstructural proteins of the Flavivirus family, and with the pestiviruses (which are now also considered to be part of the Flavivirus family).

Intramuscular inoculation of polynucleotide constructs, i.e., DNA plasmids encoding proteins have been shown to result in the in situ generation of the protein in muscle cells. By using cDNA plasmids encoding viral proteins, both antibody and CTL responses were generated, providing homologous and heterologous protection against subsequent challenge with either the homologous or cross-strain protection, respectively. Each of these types of immune responses offers a potential advantage over existing vaccination strategies. The use of PNVs (polynucleotide vaccines) to generate antibodies may result in an increased duration of the antibody responses as well as the provision of an antigen that can have both the exact sequence of the clinically circulating strain of virus as well as the proper post-translational modifications and conformation of the native protein (vs. a recombinant protein). The generation of CTL responses by this means offers the benefits of cross-strain protection without the use of a live potentially pathogenic vector or attenuated virus.

Therefore, this invention contemplates methods for introducing nucleic acids into living tissue to induce expression of proteins. The invention provides a method for introducing viral proteins into the antigen processing pathway to generate virus-specific immune responses including, but not limited to, CTLs. Thus, the need for specific therapeutic agents capable of eliciting desired prophylactic immune responses against viral pathogens is met for HCV virus by this invention. Of particular importance in this therapeutic approach is the ability to induce T-cell immune responses which can prevent infections even of virus strains which are heterologous to the strain from which the antigen gene was obtained. Therefore, this invention provides DNA constructs encoding viral proteins of the hepatitis C virus core, envelope (E1), nonstructural (NS5) genes or any other HCV genes which encode products which generate specific immune responses including but not limited to CTLs.

DNA Vaccines

Benvenisty, N., and Reshef, L. [PNAS 83, 9551–9555, (1986)] showed that $CaCl_2$-precipitated DNA introduced into mice intraperitoneal ly (i.p.), intravenously (i.v.) or intramuscularly (i.m.) could be expressed. The i.m. injection of DNA expression vectors without $CaCl_2$ treatment in mice resulted in the uptake of DNA by the muscle cells and expression of the protein encoded by the DNA. The plasmids were maintained episomally and did not replicate. Subsequently, persistent expression has been observed after i.m. injection in skeletal muscle of rats, fish and primates, and cardiac muscle of rats. The technique of using nucleic acids as therapeutic agents was reported in WO90/11092 (Oct. 4, 1990), in which polynucleotides were used to vaccinate vertebrates.

It is not necessary for the success of the method that immunization be intramuscular. The introduction of gold microprojectiles coated with DNA encoding bovine growth hormone (BGH) into the skin of mice resulted in production of anti-BGH antibodies in the mice. A jet injector has been used to transfect skin, muscle, fat, and mammary tissues of living animals. Various methods for introducing nucleic acids have been reviewed. Intravenous injection of a DNA-:cationic liposome complex in mice was shown by Zhu et al., [Science 261:209–211 (Jul. 9, 1993) to result in systemic expression of a cloned transgene. Ulmer et al., [Science 259:1745–1749, (1993)] reported on the heterologous protection against influenza virus infection by intramuscular injection of DNA encoding influenza virus proteins.

The need for specific therapeutic and prophylactic agents capable of eliciting desired immune responses against pathogens and tumor antigens is met by the instant invention. Of particular importance in this therapeutic approach is the ability to induce T-cell immune responses which can prevent infections or disease caused even by virus strains which are heterologous to the strain from which the antigen gene was obtained. This is of particular concern when dealing with HIV as this virus has been recognized to mutate rapidly and many virulent isolates have been identified [see, for example, LaRosa et al., Science 249:932–935 (1990), identifying 245 separate HIV isolates]. In response to this recognized diversity, researchers have attempted to generate CTLs based on peptide immunization. Thus, Takahashi et al., [Science 255:333–336 (1992)] reported on the induction of broadly cross-reactive cytotoxic T cells recognizing an HIV envelope (gp160) determinant. However, those workers recognized the difficulty in achieving a truly cross-reactive CTL response and suggested that there is a dichotomy between the priming or restimulation of T cells, which is very stringent, and the elicitation of effector function, including cytotoxicity, from already stimulated CTLs.

Wang et al. reported on elicitation of immune responses in nice against HIV by intramuscular inoculation with a cloned, genomic (unspliced) HIV gene. However, the level of immune responses achieved in these studies was very low. In addition, the Wang et al., DNA construct utilized an essentially genomic piece of HIV encoding contiguous Tat/REV-gp160-Tat/REV coding sequences. As is described in detail below, this is a suboptimal system for obtaining high-level expression of the gp160. It also is potentially dangerous because expression of Tat contributes to the progression of Karposi's Sarcoma.

WO 93/17706 describes a method for vaccinating an animal against a virus, wherein carrier particles were coated with a gene construct and the coated particles are accelerated into cells of an animal.

The instant invention contemplates any of the known methods for introducing polynucleotides into living tissue to induce expression of proteins. However, this invention provides a novel immunogen for introducing proteins into the antigen processing pathway to efficiently generate specific CTLs and antibodies.

Codon Usage and Codon Context

The codon pairings of organisms are highly nonrandom, and differ from organism to organism. This information is used to construct and express altered or synthetic genes having desired levels of translational efficiency, to determine which regions in a genome are protein coding regions, to introduce translational pause sites into heterologous genes, and to ascertain relationship or ancestral origin of nucleotide sequences The expression of foreign heterologous genes in transformed organisms is now commonplace. A large number of mammalian genes, including, for example, murine and human genes, have been successfully inserted into single celled organisms. Standard techniques in this regard include introduction of the foreign gene to be expressed into a vector such as a plasmid or a phage and utilizing that vector to insert the gene into an organism. The native promoters for such genes are commonly replaced with strong promoters compatible with the host into which the gene is inserted. Protein sequencing machinery permits elucidation of the amino acid sequences of even minute quantities of native protein. From these amino acid sequences, DNA sequences coding for those proteins can be inferred. DNA synthesis is also a rapidly developing art, and synthetic genes corresponding to those inferred DNA sequences can be readily constructed.

Despite the burgeoning knowledge of expression systems and recombinant DNA, significant obstacles remain when one attempts to express a foreign or synthetic gene in an organism. Many native, active proteins, for example, are glycosylated in a manner different from that which occurs when they are expressed in a foreign host. For this reason, eukaryotic hosts such as yeast may be preferred to bacterial hosts for expressing many mammalian genes. The glycosylation problem is the subject of continuing research.

Another problem is more poorly understood. Often translation of a synthetic gene, even when coupled with a strong promoter, proceeds much less efficiently than would be expected. The same is frequently true of exogenous genes foreign to the expression organism. Even when the gene is transcribed in a sufficiently efficient manner that recoverable quantities of the translation product are produced, the protein is often inactive or otherwise different in properties from the native protein.

It is recognized that the latter problem is commonly due to differences in protein folding in various organisms. The solution to this problem has been elusive, and the mechanisms controlling protein folding are poorly understood.

The problems related to translational efficiency are believed to be related to codon context effects. The protein coding regions of genes in all organisms are subject to a wide variety of functional constraints, some of which depend on the requirement for encoding a properly functioning protein, as well as appropriate translational start and stop signals. However, several features of protein coding regions have been discerned which are not readily understood in terms of these constraints. Two important classes of such features are those involving codon usage and codon context.

It is known that codon utilization is highly biased and varies considerably between different organisms. Codon usage patterns have been shown to be related to the relative abundance of tRNA isoacceptors. Genes encoding proteins of high versus low abundance show differences in their codon preferences. The possibility that biases in codon usage alter peptide elongation rates has been widely discussed. While differences in codon use are associated with differences in translation rates, direct effects of codon choice on translation have been difficult to demonstrate. Other proposed constraints on codon usage patterns include maximizing the fidelity of translation and optimizing the kinetic efficiency of protein synthesis.

Apart from the non-random use of codons, considerable evidence has accumulated that codon/anticodon recognition is influenced by sequences outside the codon itself, a phenomenon termed "codon context." There exists a strong influence of nearby nucleotides on the efficiency of suppression of nonsense codons as well as missense codons. Clearly, the abundance of suppressor activity in natural bacterial populations, as well as the use of "termination" codons to encode selenocysteine and phosphoserine require that termination be context-dependent. Similar context effects have been shown to influence the fidelity of translation, as well as the efficiency of translation initiation.

Statistical analyses of protein coding regions of *E. coli* have demonstrate another manifestation of "codon context." The presence of a particular codon at one position strongly influences the frequency of occurrence of certain nucleotides in neighboring codons, and these context constraints differ markedly for genes expressed at high versus low levels. Although the context effect has been recognized, the predictive value of the statistical rules relating to preferred nucleotides adjacent to codons is relatively low. This has limited the utility of such nucleotide preference data for selecting codons to effect desired levels of translational efficiency.

The advent of automated nucleotide sequencing equipment has made available large quantities of sequence data for a wide variety of organisms. Understanding those data presents substantial difficulties. For example, it is important to identify the coding regions of the genome in order to relate the genetic sequence data to protein sequences. In addition, the ancestry of the genome of certain organisms is of substantial interest. It is known that genomes of some organisms are of mixed ancestry. Some sequences that are viral in origin are now stably incorporated into the genome of eukaryotic organisms. The viral sequences themselves may have originated in another substantially unrelated species. An understanding of the ancestry of a gene can be important in drawing proper analogies between related genes and their translation products in other organisms.

There is a need for a better understanding of codon context effects on translation, and for a method for determining the appropriate codons for any desired translational effect. There is also a need for a method for identifying coding regions of the genome from nucleotide sequence data. There is also a need for a method for controlling protein folding and for insuring that a foreign gene will fold appropriately when expressed in a host. Genes altered or constructed in accordance with desired translational efficiencies would be of significant worth.

Another aspect of the practice of recombinant DNA techniques for the expression by microorganisms of proteins of industrial and pharmaceutical interest is the phenomenon of "codon preference". While it was earlier noted that the existing machinery for gene expression is genetically transformed host cells will "operate" to construct a given desired product, levels of expression attained in a microorganism can be subject to wide variation, depending in part on specific alternative forms of the amino acid-specifying genetic code present in an inserted exogenous gene. A "triplet" codon of four possible nucleotide bases can exist in 64 variant forms. That these forms provide the message for only 20 different amino acids (as well as transcription initiation and termination) means that some amino acids can be coded for by more than one codon. Indeed, some amino acids have as many as six "redundant", alternative codons while some others have a single, required codon. For reasons not completely understood, alternative codons are not at all uniformly present in the endogenous DNA of differing types of cells and there appears to exist a variable natural hierarchy or "preference" for certain codons in certain types of cells.

As one example, the amino acid leucine is specified by any of six DNA codons including CTA, CTC, CTG, CTT, TTA, and TTG (which correspond, respectively, to the mRNA codons, CUA, CUC, CUG, CUU, UUA and UUG). Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally held that the likelihood of obtaining high levels of expression of a leucine-rich polypeptide by an *E. coli* host will depend to some extent on the frequency of codon use. For example, a gene rich in TTA codons will in all probability be poorly expressed in *E. coli,* whereas a CTG ricb gene will probably highly express the polypeptide. Similarly, when yeast cells are the projected transformation host cells for expression of a leucine-rich polypeptide, a preferred codon for use in an inserted DNA would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide a preferred form of foreign genetic material for practice of recombinant DNA techniques.

Protein Trafficking

The diversity of function that typifies eukaryotic cells depends upon the structural differentiation of their membrane boundaries. To generate and maintain these structures, proteins must be transported from their site of synthesis in the endoplasmic reticulum to predetermined destinations throughout the cell. This requires that the trafficking proteins display sorting signals that are recognized by the molecular machinery responsible for route selection located at the access points to the main trafficking pathways. Sorting decisions for most proteins need to be made only once as they traverse their biosynthetic pathways since their final destination, the cellular location at which they perform their function, becomes their permanent residence.

Maintenance of intracellular integrity depends in part on the selective sorting and accurate transport of proteins to their correct destinations. Over the past few years the dissection of the molecular machinery for targeting and localization of proteins has been studied vigorously. Defined sequence motifs have been identified on proteins which can act as 'address labels'. A number of sorting signals have been found associated with the cytoplasmic domains of membrane proteins.

SUMMARY OF THE INVENTION

This invention relates to novel formulations of nucleic acid pharmaceutical products, specifically nucleic acid vaccine products. The nucleic acid products, when introduced directly into muscle cells, induce the production of immune responses which specifically recognize Hepatitis C virus (HCV).

BRIEF DESCRIPTION OF THE DRAWINGS

FIGS. 1A and 1B show the nucleotide sequence (SEQ. ID. NO. 1) of the V1Ra vector.

FIG. 5 shows an optimized nucleotide sequence (SEQ. ID. NO. 2) of the HCV core antigen and the encoded amino acid sequence (SEQ. ID. NO. 3).

FIG. 7 shows the Hepatitis C Virus Core Antigen nucleotide sequence (SEQ. ID. NO. 5) and amino acid sequence (SEQ. ID. NO. 3).

FIG. 8 shows codon utilization in human protein-coding sequences (from Lathe et al.).

FIG. 9 shows an optimized nucleotide sequence (SEQ. ID. NO. 6) and the encoded amino acid sequence (SEQ. ID. NO. 7) of the HCV E1 protein.

FIGS. 10A and 10B show an optimized nucleotide sequence (SEQ. ID. NO. 8) and the encoded amino acid sequence (SEQ. ID. NO. 9) of the HCV E2 protein.

FIGS. 11A, 11B and 11C show an optimized nucleotide sequence (SEQ. ID. NO. 10) and the encoded amino acid sequence (SEQ. ID. NO. 11) of the HCV E1+E2 proteins.

FIGS. 12A, 12B and 12C show an optimized nucleotide sequence (SEQ. ID. NO. 12) and the encoded amino acid sequence (SEQ. ID. NO. 13) of the HCV NS5a protein.

FIGS. 13A, 13B, 13C and 13D show an optimized nucleotide sequence (SEQ. ID. NO. 14) and the encoded amino acid sequence (SEQ. ID. NO. 15) of the HCV NS5b protein.

DETAILED DESCRIPTION OF THE INVENTION

Figure 2:
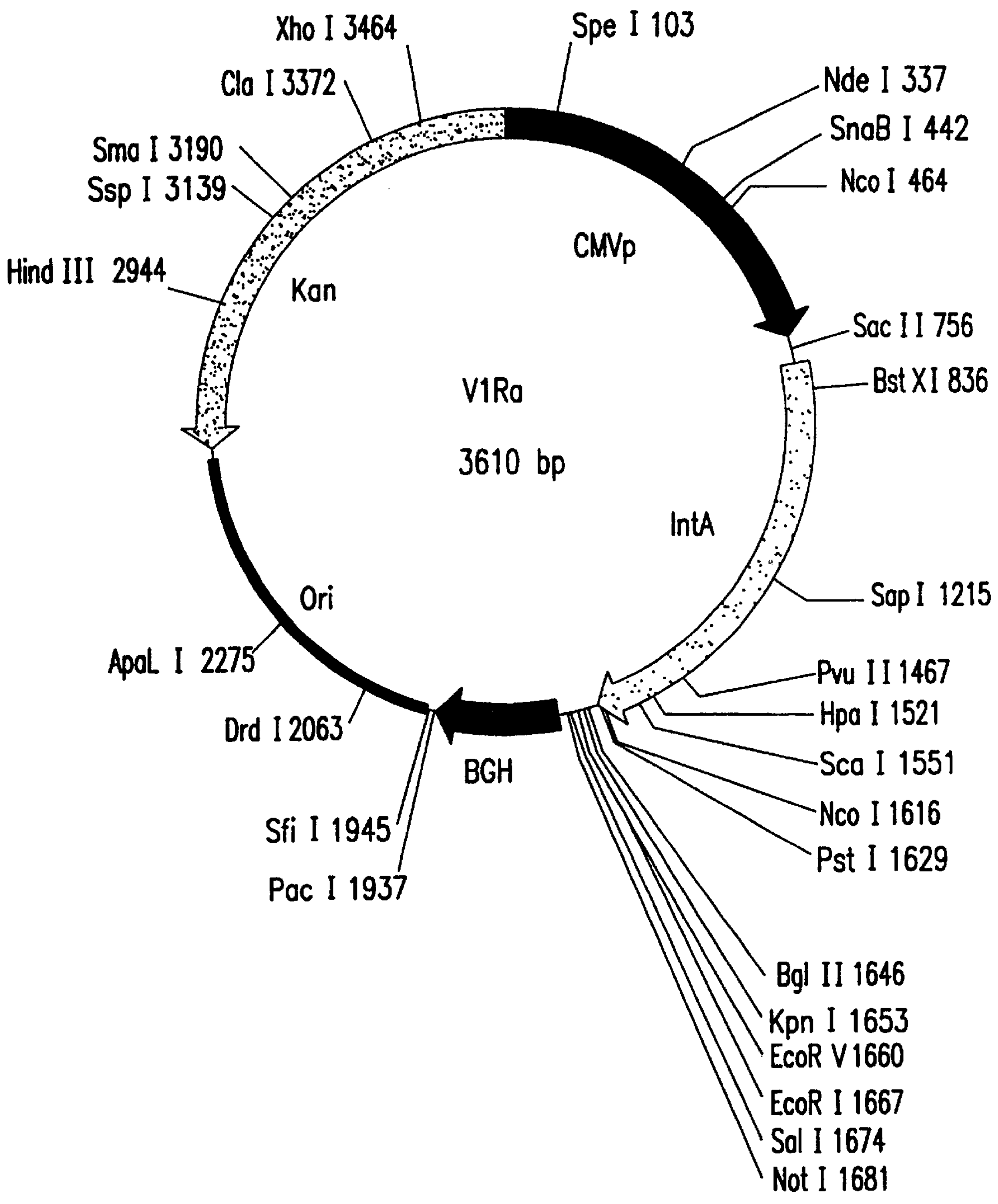
FIG. 2 is a diagram of the V1Ra vector.

This invention relates to novel fonnulations of nucleic acid pharmaceutical products, specifically nucleic acid vaccine products. The nucleic acid vaccine products, when introduced directly into muscle cells, induce the production of immune responses which specifically recognize Hepatitis C virus (HCV).

Non-A, Non-B hepatitis (NANBH) is a transmissible disease (or family of diseases) that is believed to be virally induced, and is distinguishable from other forms of virus-associated liver disease, such as those caused by hepatitis A virus (HAV), hepatitis B virus (HBV), delta hepatitis virus (HDV), cytomegalovirus (CMV) or Epstein-Barr virus (EBV). Epidemiologic evidence suggests that there may be three types of NANBH: the water-bome epidemic type; the blood or needle associated type; and the sporadically occurring (community acquired) type. However, the number of causative agents is unknown. Recently, a new viral species, hepatitis C virus (HCV) has been identified as the primary (if not only) cause of blood-associated NANBH (BB-NANBH). Hepatitis C appears to be the major form of transfusion-associated hepatitis in a number of countries, including the United States and Japan. There is also evidence implicating HCV in induction of hepatocellular carcinoma. Thus, a need exists for an effective method for preventing or treating HCV infection: currently, there is none.

The HCV may be distantly related to the flaviviridae. The Flavivirus family contains a large number of viruses which are small, enveloped pathogens of man. The morphology and composition of Flavivirus particles are known, and are discussed in M. A. Brinton, in “The Viruses: The Togaviridae And Flaviviridae” (Series eds. Fraenkel-Conrat and Wagner, vol. eds. Schlesinger and Schlesinger, Plenum Press, 1996), pp. 327–374. Generally, with respect to morphology, Flaviviruses contain a central nucleocapsid surrounded by a lipid bilayer. Virions are spherical and have a diameter of about 40–50 nm. Their cores are about 25–30 nm in diameter. Along the outer surface of the virion envelope are projections measuring about 5–10 nm in length with terminal knobs about 2 nm in diameter. Typical examples of the family include Yellow Fever virus, West Nile virus, and Dengue Fever virus. They possess positive-stranded RNA genomes (about 11,000 nucleotides) that are slightly larger than that of HCV and encode a polyprotein precursor of about 3500 amino acids. Individual viral proteins are cleaved from this precursor polypeptide.

The genome of HCV appears to be single-stranded RNA containing about 10,000 nucleotides. The genome is positive-stranded, and possesses a continuous translational open reading frame (ORF) that encodes a polyprotein of about 3,000 amino acids. In the ORF, the structural proteins appear to be encoded in approximately the first quarter of the N-terminal region, with the majority of the polyprotein attributed to non-structural proteins. When compared with all known viral sequences, small but significant co-linear homologies are observed with the nonstructural proteins of the Flavivirus family, and with the pestiviruses (which are now also considered to be part of the Flavivirus family).

Intramuscular inoculation of polynucleotide constructs, i.e., DNA plasmids encoding proteins halve been shown to result in the generation of the encoded protein in situ in muscle cells. By using cDNA plasmids encoding viral proteins, both antibody and CTL responses were generated, providing homologous and heterologous protection against subsequent challenge with either the homologous or cross-strain protection, respectively. Each of these types of immune responses offers a potential advantage over existing vaccination strategies. The use of PNVs (polynucleotide vaccines) to generate antibodies may result in an increased duration of the antibody responses as well as the provision of an antigen that can have both the exact sequence of the clinically circulating strain of virus as well as the proper post-translational modifications and conformation of the native protein (vs. a recombinant protein). The generation of CTL responses by this means offers the benefits of cross-strain protection without the use of a live potentially pathogenic vector or attenuated virus.

The standard techniques of molecular biology for preparing and purifying DNA constructs enable the preparation of the DNA therapeutics of this invention. While standard techniques of molecular biology are therefore sufficient for the production of the products of this invention, the specific constructs disclosed herein provide novel therapeutics which surprisingly produce cross-strain protection, a result heretofore unattainable with standard inactivated whole virus or subunit protein vaccines.

The amount of expressible DNA to be introduced to a vaccine recipient will depend on the strength of the transcriptional and translational promoters used in the DNA construct, and on the immunogenicity of the expressed gene product. In general, an immunologically or prophylactically effective dose of about 1 $\mu$g to 1 mg, and preferably about 10 $\mu$g to 300 $\mu$g is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided.

The DNA may be naked, that is, unassociated with any proteins, adjuvants or other agents which impact on the recipients immune system. In this case, it is desirable for the DNA to be in a physiologically acceptable solution, such as, but not limited to, sterile saline or sterile buffered saline. Alternatively, the DNA may be associated with surfactants, liposomes, such as lecithin liposomes or other liposomes known in the art, as a DNA-liposome mixture, (see for example WO93/24640) or the DNA may be associated with an adjuvant known in the art to boost immune responses, such as a protein or other carrier. Agents which assist in the cellular uptake of DNA, such as, but not limited to, calcium ions, detergents, viral proteins and other transfection facilitating agents may also be used to advantage. These agents are generally referred to as transfection facilitating agents and as pharmaceutically acceptable carriers. As used herein, the term gene refers to a segment of nucleic acid which encodes a discrete polypeptide. The term pharmaceutical, and vaccine are used interchangeably to indicate compositions useful for inducing immune responses. The terms construct, and plasmid are used interchangeably. The term vector is used to indicate a DNA into which genes may be cloned for use according to the method of this invention.

The following examples are provided to further define the invention, without limiting the invention to the specifics of the examples.

EXAMPLE 1

V1J Expression Vectors

V1J is derived from vectors V1 and pUC18, a commercially available plasmid. V1 was digested with SspI and EcoRI restriction enzymes producing two fragments of DNA. The smaller of these fragments, containing the CMVintA promoter and Bovine Growth Hormone (BGH) transcription termination elements which control the expression of heterologous genes, was purified from an agarose electrophoresis gel. The ends of this DNA fragment were then "blunted" using the T4 DNA polymerase enzyme in order to facilitate its ligation to another "blunt-ended" DNA fragment.

pUC18 was chosen to provide the "backbone" of the expression vector. It is known to produce high yields of plasmid, is well-characterized by sequence and function, and is of minimum size. We removed the entire lac operon from this vector, which was unnecessary for our purposes and may be detrimental to plasmid yields and heterologous gene expression, by partial digestion with the HaeII restriction enzyme. The remaining plasmid was purified from an agarose electrophoresis gel, blunt-ended with the T4 DNA polymerase, treated with calf intestinal alkaline phosphatase, and ligated to the CMVintA/BGH element described above. Plasmids exhibiting either of two possible orientations of the promoter elements within the pUC backbone were obtained. One of these plasmids gave much higher yields of DNA in *E. coli* and was designated V1J. This vector's structure was verified by sequence analysis of the junction regions and was subsequently demonstrated to give comparable or higher expression of heterologous genes compared with V1. The ampicillin resistance marker was replaced with the neomycin resistance marker to yield vector V1Jneo.

An Sfi I site was added to V1Jneo to facilitate integration studies. A commercially available 13 base pair Sfi I linker (New England BioLabs) was added at the Kpn I site within the BGH sequence of the vector. V1Jneo was linearized with Kpn I, gel purified, blunted by T4 DNA polymerase, and ligated to the blunt Sfi I linker. Clonal isolates were chosen by restriction mapping and verified by sequencing through the linker. The new vector was designated V1Jns. Expression of heterologous genes in V1Jns (with Sfi I) was comparable to expression of the same genes in V1Jneo (with Kpn I).

Figure 3:
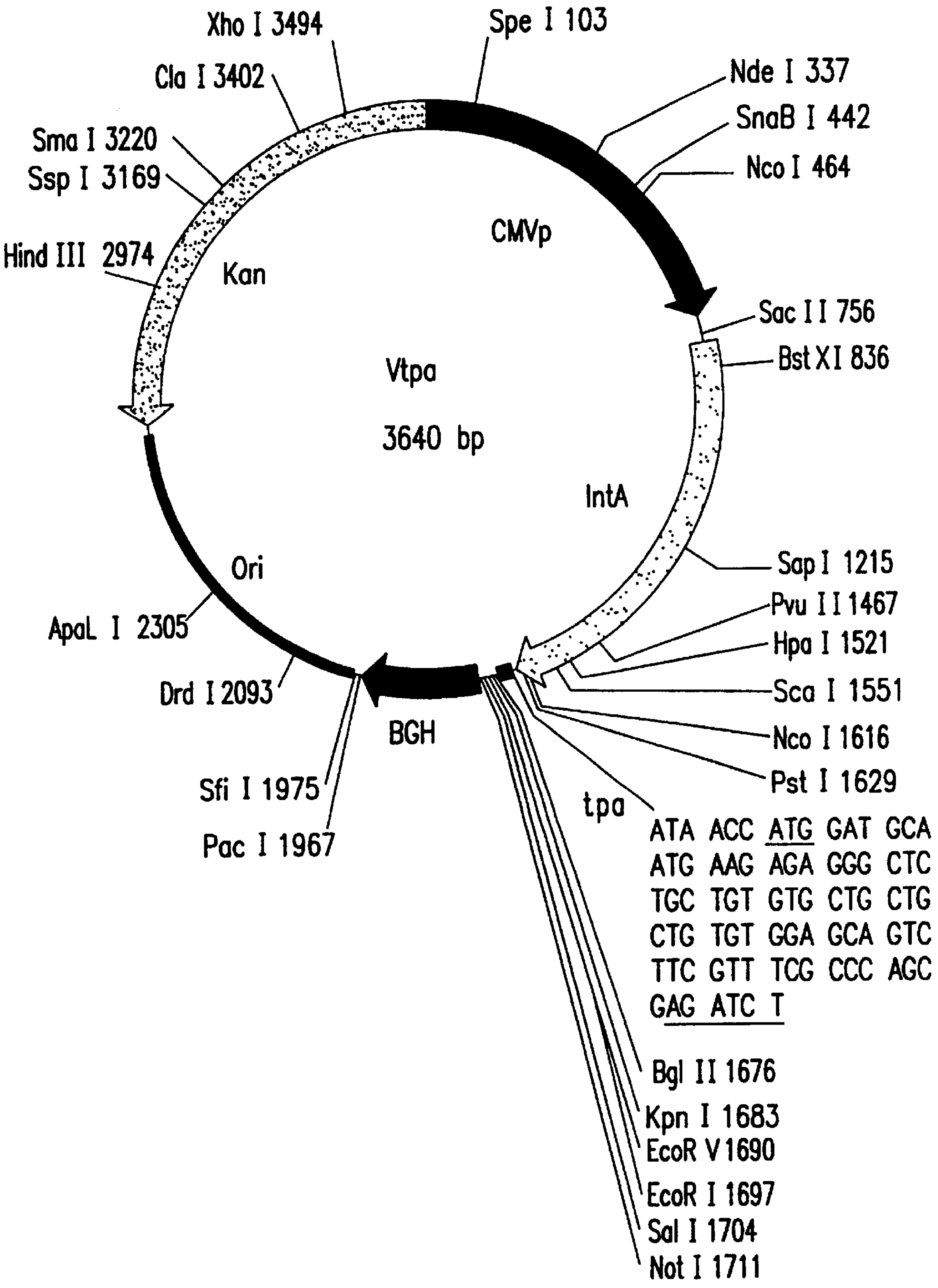
FIG. 3 is a diagram of the Vtpa vector.
Figure 4:
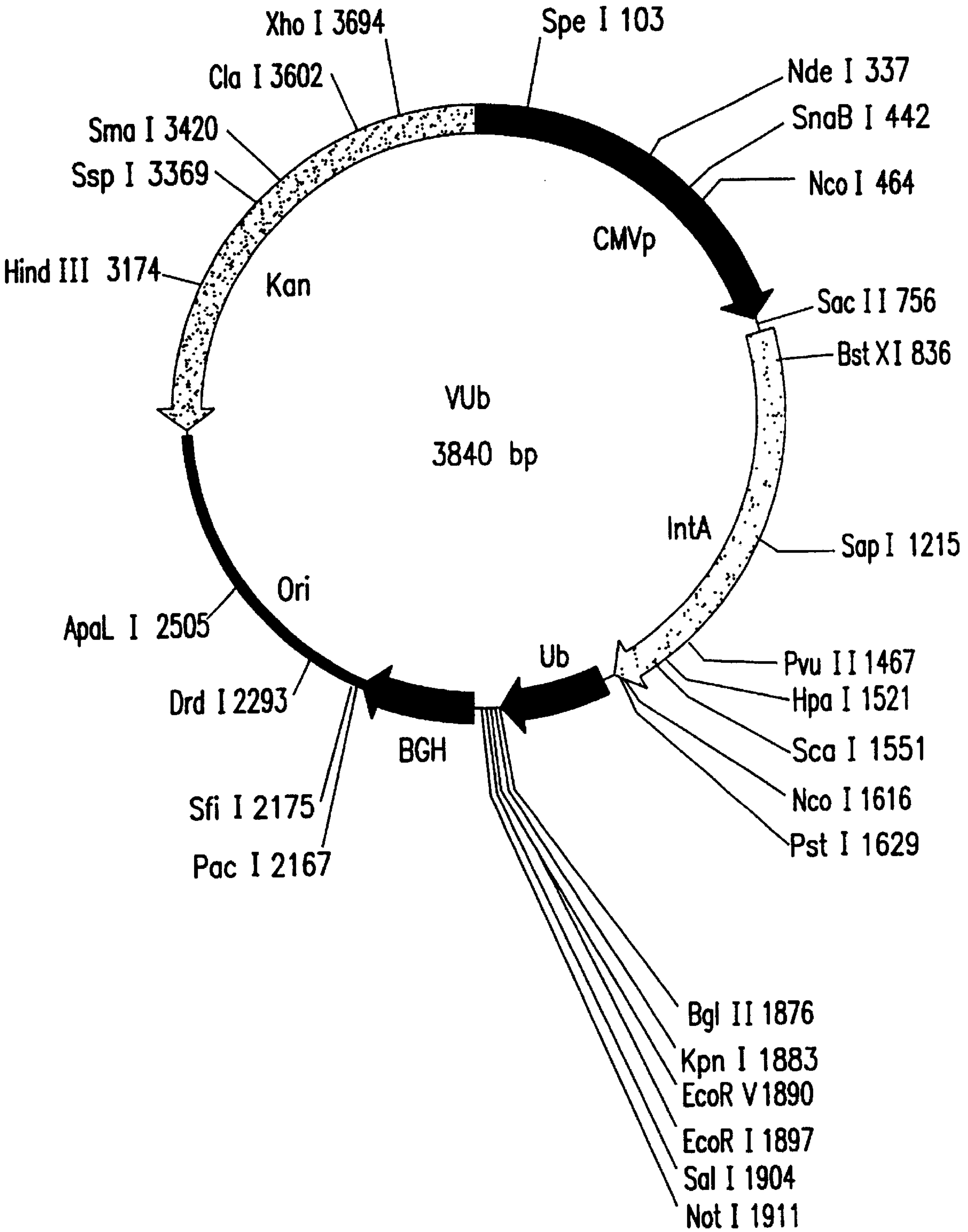
FIG. 4 is the VUb vector.

Vector V1Ra (Sequence is shown in FIG. 1; map is shown in FIG. 2) was derived from vector V1R, a derivative of the V1Jns vector. Multiple cloning sites (BglII, KpnI, EcoRV, EcoRI, SalI, and NotI) were introduced into V1R to create the V1Ra vector to improve the convenience of subcloning. V1Ra vector derivatives containing the tpa leader sequence and ubiquitin sequence were generated (Vtpa (FIG. 3) and Vub (FIG. 4), respectively). Expression of viral antigen from Vtpa vector will target the antigen protein into the exocytic pathway, thus producing a secretable form of the antigen proteins. These secreted proteins are likely to be captured by professional antigen presenting cells, such as macrophages and dendritic cells, and processed and presented by class II molecules to activate CD4+ Th cells. They also are more likely to efficiently simulate antibody responses. Expression of viral antigen through VUb vector will produce a ubiquitin and antigen fusion protein. The uncleavable ubiquitin segment (glycine to alanine change at the cleavage site, Butt et al., JBC 263:16364, 1988) will target the viral antigen to ubiquitin-associated proteasomes for rapid degradation. The resulting peptide fragments will be transported into the ER for antigen presentation by class I molecules. This modification is attempted to enhance the class I molecule-restricted CTL responses against the viral antigen (Townsend et al, JEM 168:1211, 1988).

EXAMPLE 2

Design and Construction of the Synthetic Genes

A. Design of Synthetic Gene Sepments for HCV Gene Expression

Gene segments were converted to sequences having identical translated sequences (except where noted) but with alternative codon usage as defined by R. Lathe in a research article from *J. Molec. Biol. Vol.* 183, pp. 1–12 (1985) entitled "Synthetic Oligonucleotide Probes Deduced from Amino Acid Sequence Data: Theoretical and Practical Considerations". The methodology described below was based on our hypothesis that the known inability to express a gene efficiently in mammalian cells is a consequence of the overall transcript composition. Thus, using alternative codons encoding the same protein sequence may remove the constraints on HCV gene expression. Inspection of the codon usage within HCV genome revealed that a high percentage of codons were among those infrequently used by highly expressed human genes. The specific codon replacement method employed may be described as follows employing data from Lathe et al.:

1. Identify placement of codons for proper open reading frame.
2. Compare wild type codon for observed frequency of use by human genes (refer to Table 3 in Lathe et al.).
3. If codon is not the most commonly employed, replace it with an optimal codon for high expression based on data in Table 5.
4. Inspect the third nucleotide of the new codon and the first nucleotide of the adjacent codon immediately 3'- of the first. If a 5'-CG-3' pairing has been created by the new codon selection, replace it with the choice indicated in Table 5.
5. Repeat this procedure until the entire gene segment has been replaced.
6. Inspect new gene sequence for undesired sequences generated by these codon replacements (e.g., "ATTTA" sequences, inadvertent creation of intron splice recognition sites, unwanted restriction enzyme sites, etc.) and substitute codons that eliminate these sequences.

7. Assemble synthetic gene segments and test for improved expression.

B. HCV Core Antigen Sequence

The consensus core sequence of HCV was adopted from a generalized core sequence reported by Bukh et al. (PNAS, 91:8239, 1994). This core sequence contains all the identified CTL epitopes in both human and mouse. The gene is composed of 573 nucleotides and encodes 191 amino acids. The predicted molecular weight is about 23 kDa.

The codon replacement was conducted to eliminate codons which may hinder the expression of the HCV core protein in transfected mammalian cells in order to maximize the translational efficiency of DNA vaccine. Twenty three point two percent (23.2%) of nucleotide sequence (133 out of 573 nucleotides) were altered, resulting in changes of 61.3% of the codons (117 out 191 codons) in the core antigen sequence. The optimized nucleotide sequence of HCV core is shown in FIG. 5.

C. Construction of the Synthetic Core Gene

Figure 6:
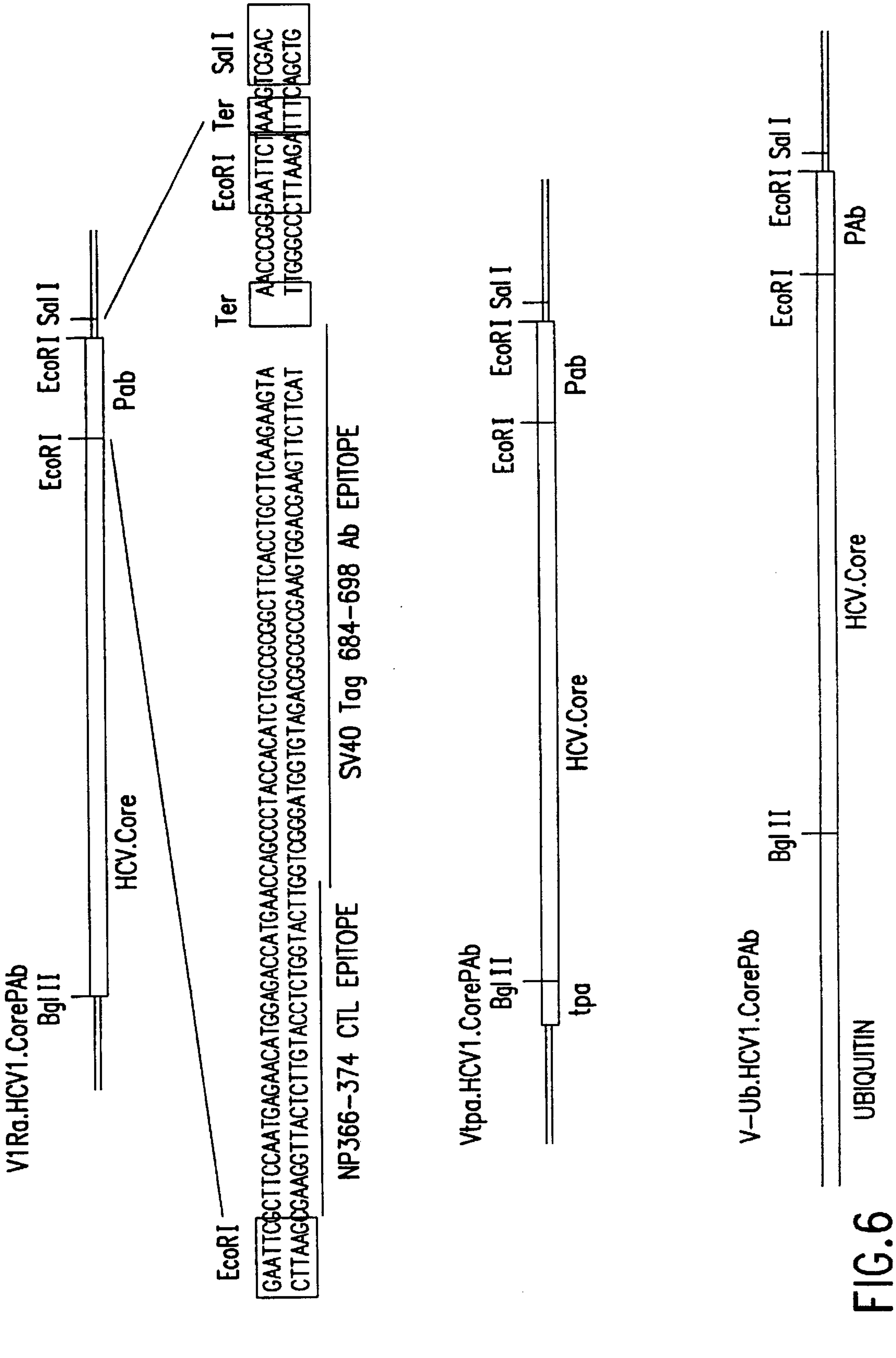
FIG. 6 shows V1Ra.HCV1CorePAb, Vtpa.HCV1CorePAb and VUb.HCV1CorePAb. A sequence coding for an epitope derived from influenza virus nucleoprotein residues 366–374 and an antibody epitope sequence derived from SV40 T antigen resides 684–698 is illustrated by SEQ. ID. NO. 4 (starting GAA) and its complementary sequence SEQ. ID. NO. 16 (starting CTT).

The optimized HCV core gene (FIG. 5) was constructed as a synthetic gene annealed from multiple synthetic oligonucleotides. To facilitate the identification and evaluation of the synthetic gene expression in cell culture and its immunogenicity in mice, a CTL epitope derived from influenza virus nucleoprotein residues 366–374 and an antibody epitope sequence derived from SV40 T antigen residues 684–699 were tagged to the carboxyl terminal of the core sequence (FIG. 6). For clinical use it may be desired to express the core sequence without the nucleoprotein 366–374 and SV40 T 684–698 sequences. For this reason, the sequence of the two epitopes is flanked by two EcoRI sites which will be used to excise this fragment of sequence at a later time. Thus an embodiment of the invention for clinical use could consist of the V1Ra.HCV1CorePAb, Vtpa.HCV1CorePAb, or VUb.HCV1CorePAb plasmids that had been cut with EcoRI, annealed, and ligated to yield plasmids V1Ra.HCV1Core, Vtpa.HCV1Core, and VUb.HCV1Core.

The synthetic gene was built as three separate segments in three vectors, nucleotides 1 to 80 in V1Ra, nucleotides 80 to 347 (BstX1 site) in pUC18, and nucleotides 347 to 573 plus the two epitope sequence in pUC18. All the segments were verified by DNA sequencing, and joined together in V1Ra vector.

D. HCV Gene Expression Constructs

In each case, the junction sequences from the 5' promoter region (CMVintA) into the cloned gene is shown. The position at which the junction occurs is demarcated by a "/", which does not represent any discontinuity in the sequence.

The nomenclature for these constructs follows the convention: "Vector name-HCV strain-gene".

```
V1Ra.HICV1.CorePAb
---IntA--AGA TCT ACC ATG AGC (SEQ. ID. NO.
17)--HCV.Core.--GCC GAA TTC GCT TCC (SEQ. ID. NO.
18)--PAb Sequence--TAA ACC CGG GAA TTC TAA A GTC
GAC (SEQ. ID. NO. 19)--BGH---

Vtpa.HCV1.CorePAb
---IntA--ATC ACC ATG GAT (SEQ. ID. NO. 20)--tpa
leader--GAG ATC-TTC ATG AGC (SEQ. ID. NO. 21)--
HCV.Core.--GCC GAA TTC GCT TCC--(SEQ. ID. NO.
18) PAb Sequence--TAA ACC CGG GAA TTC TAA A GTC
GAC (SEQ. ID. NO. 19)--BGH---

VUb.HCV1.CorePAb.
---IntA--AGA TCC ACC ATG CAG (SEQ. ID. NO. 22)
--Ubiquitin--GGT GCA GAT CTG ATG AGC (SEQ. ID. NO.
23)--HCV.Core.--GCC GAA TTC GCT TCC--(SEQ. ID. NO.
18) PAb Sequence--TAA ACC CGG GAA TTC TAA A GTC
GAC--BGH--

V1Ra.HCV1.Core
---IntA--AGA TCT ACC ATG AGC (SEQ. ID. NO. 17)--
HCV.Core.--GCC TAA A GTC GAC (SEQ. ID. NO. 24)--
BGH---

Vtpa.HCV1.Core
---IntA--ATC ACC ATG GAT (SEQ. ID. NO. 20)--tpa
leader--GAG ATC-TTC ATG AGC (SEQ. ID. NO. 21)--
HCV.Core.--GCC TAA A GTC GAC (SEQ. ID. NO. 24)--
BGH---

VUb.HCV1.Core
---IntA--AGA TCC ACC ATG CAG (SEQ. ID. NO. 22)--
Ubiquitin--GGT GCA GAT CTG ATG AGC (SEQ. ID. NO.
23)--HCV.Core.--GCC TAA A GTC GAC (SEQ. ID. NO.
24)--BGH--
```

E. Other Synthetic HCV Genes

Using similar codon optimization techniques, synthetic genes encoding the HCV E1 (FIG. 9), HCV E2 (FIG. 10), HCV E1+E2 (FIG. 11), HCV NS5a (FIG. 12) and HCV NS5b (FIG. 13) proteins were created.

SEQUENCE LISTING

```
<160> NUMBER OF SEQ ID NOS: 25

<210> SEQ ID NO 1
<211> LENGTH: 3610
<212> TYPE: DNA
<213> ORGANISM: Artificial Sequence
<220> FEATURE:
<223> OTHER INFORMATION: Modified Vector Sequence

<400> SEQUENCE: 1

gatattggct attggccatt gcatacgttg tatccatatc ataatatgta catttatatt    60

ggctcatgtc caacattacc gccatgttga cattgattat tgactagtta ttaatagtaa   120

tcaattacgg ggtcattagt tcatagccca tatatggagt tccgcgttac ataacttacg   180

gtaaatggcc cgcctggctg accgcccaac gacccccgcc cattgacgtc aataatgacg   240

tatgttccca tagtaacgcc aatagggact ttccattgac gtcaatgggt ggagtattta   300
```

-continued

```
cggtaaactg cccacttggc agtacatcaa gtgtatcata tgccaagtac gccccctatt   360
gacgtcaatg acggtaaatg gcccgcctgg cattatgccc agtacatgac cttatgggac   420
tttcctactt ggcagtacat ctacgtatta gtcatcgcta ttaccatggt gatgcggttt   480
tggcagtaca tcaatgggcg tggatagcgg tttgactcac ggggatttcc aagtctccac   540
cccattgacg tcaatgggag tttgttttgg caccaaaatc aacgggactt tccaaaatgt   600
cgtaacaact ccgccccatt gacgcaaatg ggcggtaggc gtgtacggtg ggaggtctat   660
ataagcagag ctcgtttagt gaaccgtcag atcgcctgga gacgccatcc acgctgtttt   720
gacctccata gaagacaccg ggaccgatcc agcctccgcg gccgggaacg gtgcattgga   780
acgcggattc cccgtgccaa gagtgacgta agtaccgcct atagagtcta taggcccacc   840
cccttggctt cttatgcatg ctatactgtt tttggcttgg ggtctataca cccccgcttc   900
ctcatgttat aggtgatggt atagcttagc ctataggtgt gggttattga ccattattga   960
ccactcccct attggtgacg atactttcca ttactaatcc ataacatggc tctttgccac  1020
aactctcttt attggctata tgccaataca ctgtccttca gagactgaca cggactctgt  1080
atttttacag gatggggtct catttattat ttacaaattc acatatacaa caccaccgtc  1140
cccagtgccc gcagttttta ttaaacataa cgtgggatct ccacgcgaat ctcgggtacg  1200
tgttccggac atgggctctt ctccggtagc ggcggagctt ctacatccga gccctgctcc  1260
catgcctcca gcgactcatg gtcgctcggc agctccttgc tcctaacagt ggaggccaga  1320
cttaggcaca gcacgatgcc caccaccacc agtgtgccgc acaaggccgt ggcggtaggg  1380
tatgtgtctg aaaatgagct cggggagcgg gcttgcaccg ctgacgcatt tggaagactt  1440
aaggcagcgg cagaagaaga tgcaggcagc tgagttgttg tgttctgata agagtcagag  1500
gtaactcccg ttgcggtgct gttaacggtg gagggcagtg tagtctgagc agtactcgtt  1560
gctgccgcgc gcgccaccag acataatagc tgacagacta acagactgtt cctttccatg  1620
ggtcttttct gcagtcaccg tccttagatc taggtaccag atatcagaat tcagtcgaca  1680
gcggccgcga tctgctgtgc cttctagttg ccagccatct gttgtttgcc cctcccccgt  1740
gccttccttg accctggaag gtgccactcc cactgtcctt tcctaataaa atgaggaaat  1800
tgcatcgcat tgtctgagta ggtgtcattc tattctgggg ggtggggtgg ggcagcacag  1860
caagggggag gattgggaag acaatagcag gcatgctggg gatgcggtgg gctctatggg  1920
tacggccgca gcggccttaa ttaaggccgc agcggccgta cccaggtgct gaagaattga  1980
cccggttcct cgacccgtaa aaaggccgcg ttgctggcgt ttttccatag gctccgcccc  2040
cctgacgagc atcacaaaaa tcgacgctca agtcagaggt ggcgaaaccc gacaggacta  2100
taaagatacc aggcgtttcc ccctggaagc tccctcgtgc gctctcctgt tccgaccctg  2160
ccgcttaccg gatacctgtc cgcctttctc ccttcgggaa gcgtggcgct ttctcaatgc  2220
tcacgctgta ggtatctcag ttcggtgtag gtcgttcgct ccaagctggg ctgtgtgcac  2280
gaaccccccg ttcagcccga ccgctgcgcc ttatccggta actatcgtct tgagtccaac  2340
ccggtaagac acgacttatc gccactggca gcagccactg gtaacaggat tagcagagcg  2400
aggtatgtag gcggtgctac agagttcttg aagtggtggc ctaactacgg ctacactaga  2460
aggacagtat ttggtatctg cgctctgctg aagccagtta ccttcggaaa aagagttggt  2520
agctcttgat ccggcaaaca aaccaccgct ggtagcggtg gtttttttgt ttgcaagcag  2580
cagattacgc gcagaaaaaa aggatctcaa gaagatcctt tgatcttttc tacgtgatcc  2640
```

-continued cgtaatgctc tgccagtgtt acaaccaatt aaccaattct gattagaaaa actcatcgag 2700
catcaaatga aactgcaatt tattcatatc aggattatca ataccatatt tttgaaaaag 2760
ccgtttctgt aatgaaggag aaaactcacc gaggcagttc cataggatgg caagatcctg 2820
gtatcggtct gcgattccga ctcgtccaac atcaatacaa cctattaatt tcccctcgtc 2880
aaaaataagg ttatcaagtg agaaatcacc atgagtgacg actgaatccg gtgagaatgg 2940
caaaagctta tgcatttctt tccagacttg ttcaacaggc cagccattac gctcgtcatc 3000
aaaatcactc gcatcaacca aaccgttatt cattcgtgat tgcgcctgag cgagacgaaa 3060
tacgcgatcg ctgttaaaag gacaattaca aacaggaatc gaatgcaacc ggcgcaggaa 3120
cactgccagc gcatcaacaa tattttcacc tgaatcagga tattcttcta atacctggaa 3180
tgctgttttc ccggggatcg cagtggtgag taaccatgca tcatcaggag tacggataaa 3240
atgcttgatg gtcggaagag gcataaattc cgtcagccag tttagtctga ccatctcatc 3300
tgtaacatca ttggcaacgc tacctttgcc atgtttcaga aacaactctg gcgcatcggg 3360
cttcccatac aatcgataga ttgtcgcacc tgattgcccg acattatcgc gagcccattt 3420
atacccatat aaatcagcat ccatgttgga atttaatcgc ggcctcgagc aagacgtttc 3480
ccgttgaata tggctcataa cacccccttgt attactgttt atgtaagcag acagttttat 3540
tgttcatgat gatatatttt tatcttgtgc aatgtaacat cagagatttt gagacacaac 3600
gtggctttcc 3610

<210> SEQ ID NO 2
<211> LENGTH: 573
<212> TYPE: DNA
<213> ORGANISM: Artificial Sequence
<220> FEATURE:
<223> OTHER INFORMATION: Optimized sequence encoding HCV core antigen

<400> SEQUENCE: 2
atgagcacca accccaagcc ccagaggaag accaagagga acaccaacag gaggccccag 60
gatgtgaagt tccctggggg aggccagatt gtgggagggg tctacctgct gcccaggagg 120
ggccccaggc tgggggtgag ggctaccagg aagacctctg agaggtccca gcccaggggc 180
aggaggcagc ccatccccaa ggccaggagg cctgagggcc gctcctgggc ccagcctggc 240 taccccctggc ccctgtatgg caatgaaggc tttggctggg ctggctggct gctgtccccc 300
aggggctcca ggccctcctg ggccccccaca gaccccagga ggaggtccag gaacctgggc 360
aaggtgattg acaccctgac ctgtggcttt gctgacctga tgggctacat ccccctggtg 420
ggggctcctg tgggaggggt ggctagggct ctggctcatg ggtgagggt gctggaggat 480 ggggtgaact atgctactgg caacctgcct ggctgctcct tctccatctt cctgctggcc 540
ctgctctcct gcctgacagt gcctgcttct gcc 573

<210> SEQ ID NO 3
<211> LENGTH: 191
<212> TYPE: PRT
<213> ORGANISM: Hepatitis C Virus

<400> SEQUENCE: 3

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala

-continued

```
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Phe Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190
```

<210> SEQ ID NO 4
<211> LENGTH: 103
<212> TYPE: DNA
<213> ORGANISM: Artificial Sequence
<220> FEATURE:
<223> OTHER INFORMATION: Modified Vector Sequence

<400> SEQUENCE: 4

```
gaattcgctt ccaatgagaa catggagacc atgaaccagc cctaccacat ctgccgcggc    60

ttcacctgct tcaagaagta aacccgggaa ttctaaagtc gac                     103
```

<210> SEQ ID NO 5
<211> LENGTH: 573
<212> TYPE: DNA
<213> ORGANISM: Hepatitis C Virus

<400> SEQUENCE: 5

```
atgagcacga atcctaaacc tcaaagaaaa accaaacgta acaccaaccg ccgcccacag    60

gacgtcaagt tcccgggcgg tggtcagatc gttggtggag tttacttgtt gccgcgcagg   120

ggccccaggt tgggtgtgcg cgcgactagg aagacttccg agcggtcgca acctcgtgga   180

aggcgacagc ctatccccaa ggctcgccgg cccgagggca ggtcctgggc tcagcccggg   240

tacccttggc ccctctatgg caatgagggc ttcgggtggg caggatggct cctgtccccc   300

cgcggctctc ggcctagttg gggccccact gacccccggc gtaggtcgcg caatttgggt   360

aaggtcatcg ataccctcac gtgcggcttc gccgacctca tggggtacat cccgctcgtc   420

ggcgcccccg tagggggcgt cgccagggcc ctggcgcatg gcgtcagggt tctggaggac   480

ggggtgaact atgcaacagg gaatttgccc ggttgctctt tctctatctt cctcctggct   540

ctgctgtcct gcctgaccgt cccagcttct gct                                573
```

<210> SEQ ID NO 6
<211> LENGTH: 582
<212> TYPE: DNA
<213> ORGANISM: Artificial Sequence
<220> FEATURE:
<223> OTHER INFORMATION: Optimized sequence encoding HCV E1 protein -continued

<400> SEQUENCE: 6

```
atgtatgagg tgaggaatgt ctctggcgtc taccatgtga ccaatgactg ctccaactcc    60

tgcattgtct atgaggctgc tgacatgatc atgcacaccc ctggctgtgt gccatgtgtg   120

agggagggca actcctccag gtgctgggtg gccctgaccc ccaccctggc tgccaggaac   180

tcctccatcc ccaccaccac catcaggagg catgtggacc tgctggtggg cgctgctgcc   240

ctgtgctctg ccatgtatgt gggcgacctg tgtggctctg tcttcctggt gtcccagctg   300

ttcaccttct cccccaggag gtatgagact gtgcaggact gcaactgctc cctgtaccct   360

ggccatgtct ctggccacag gatggcctgg gacatgatga tgaactggtc ccccaccact   420

gccctggtgg tctcccagct gctgaggatc ccccaggctg tggtggacat ggtggtgggc   480

gcccactggg gcgtgctggc tggcctggcc tactactcca tggtgggcaa ctgggccaag   540

gtgctgattg tgatgctgct gtttgctggc gtggatggct aa                       582
```

<210> SEQ ID NO 7
<211> LENGTH: 193
<212> TYPE: PRT
<213> ORGANISM: Hepatitis C Virus

<400> SEQUENCE: 7

```
Met Tyr Glu Val Arg Asn Val Ser Gly Val Tyr His Val Thr Asn Asp
 1               5                  10                  15

Cys Ser Asn Ser Cys Ile Val Tyr Glu Ala Ala Asp Met Ile Met His
            20                  25                  30

Thr Pro Gly Cys Val Pro Cys Val Arg Glu Gly Asn Ser Ser Arg Cys
        35                  40                  45

Trp Val Ala Leu Thr Pro Thr Leu Ala Ala Arg Asn Ser Ser Ile Pro
    50                  55                  60

Thr Thr Thr Ile Arg Arg His Val Asp Leu Leu Val Gly Ala Ala Ala
65                  70                  75                  80

Leu Cys Ser Ala Met Tyr Val Gly Asp Leu Cys Gly Ser Val Phe Leu
                85                  90                  95

Val Ser Gln Leu Phe Thr Phe Ser Pro Arg Arg Tyr Glu Thr Val Gln
            100                 105                 110

Asp Cys Asn Cys Ser Leu Tyr Pro Gly His Val Ser Gly His Arg Met
        115                 120                 125

Ala Trp Asp Met Met Met Asn Trp Ser Pro Thr Thr Ala Leu Val Val
    130                 135                 140

Ser Gln Leu Leu Arg Ile Pro Gln Ala Val Val Asp Met Val Val Gly
145                 150                 155                 160

Ala His Trp Gly Val Leu Ala Gly Leu Ala Tyr Tyr Ser Met Val Gly
                165                 170                 175

Asn Trp Ala Lys Val Leu Ile Val Met Leu Leu Phe Ala Gly Val Asp
            180                 185                 190

Gly
```

<210> SEQ ID NO 8
<211> LENGTH: 1044
<212> TYPE: DNA
<213> ORGANISM: Artificial Sequence
<220> FEATURE:
<223> OTHER INFORMATION: Optimized sequence encoding HCV E2 protein

<400> SEQUENCE: 8

```
atgaccacct atgtctctgt gggccatgcc tcccagacca ccaggagggt ggcctccttc    60
```

-continued

```
ttctcccctg gctctgccca gaagatccag ctggtgaaca ccaatggctc ctggcacatc   120

aacaggactg ccctgaattg caacgagtcc atcaacactg gcttctttgc tgccctgttc   180

tatgtgaaga agttcaactc ctctggctgc tctgagagga tggcctcctg caggcccatt   240

gacaggtttg cccagggctg ggcccccatc acccatgctg agtccaggtc ctctgaccag   300

aggccatact gctggcacta tgcccccag ccatgtggca ttgtgcctgc cctgcaggtc   360

tgtggccctg tctactgctt caccccatcc cctgtggtgg tgggcaccac tgacaggttt   420

ggcgtgccca cctacaactg ggcgacaat gagactgatg tgctgctgct gaacaacacc   480

aggcccccc agggcaactg gtttggctgc acctggatga actccactgg cttcaccaag   540

acctgtggcg gccccccatg caacattggc ggcgctggca acaacaccct gacctgcccc   600

actgactgct tcaggaagca tcctgaggcc acctacacca agtgtggctc tggcccatgg   660

ctgaccccca ggtgcatggt ggactaccca tacaggctgt ggcactaccc atgcaccttc   720

aacttcacca tcttcaagat caggatgtat gtgggcggcg tggagcacag gctgaatgct   780

gcctgcaact ggaccagggg cgagaggtgc aacattgagg acagggacag gtctgagctg   840

tccccccctgc tgctgtccac cactgagtgg cagatcctgc catgctcctt caccaccctg   900

cctgccctgt ccactggcct gatccatctg catcagaaca ttgtggatgt gcagtacctg   960

tacggcgtgg gctccgctgt ggtctccatt gtgatcaagt gggagtatgt gctgctgctg  1020

ttcctgctgc tggctgatgc ctaa                                         1044
```

<210> SEQ ID NO 9
<211> LENGTH: 347
<212> TYPE: PRT
<213> ORGANISM: Hepatitis C Virus

<400> SEQUENCE: 9

```
Met Thr Thr Tyr Val Ser Val Gly His Ala Ser Gln Thr Thr Arg Arg
 1               5                  10                  15

Val Ala Ser Phe Phe Ser Pro Gly Ser Ala Gln Lys Ile Gln Leu Val
            20                  25                  30

Asn Thr Asn Gly Ser Trp His Ile Asn Arg Thr Ala Leu Asn Cys Asn
        35                  40                  45

Glu Ser Ile Asn Thr Gly Phe Phe Ala Ala Leu Phe Tyr Val Lys Lys
    50                  55                  60

Phe Asn Ser Ser Gly Cys Ser Glu Arg Met Ala Ser Cys Arg Pro Ile
65                  70                  75                  80

Asp Arg Phe Ala Gln Gly Trp Gly Pro Ile Thr His Ala Glu Ser Arg
                85                  90                  95

Ser Ser Asp Gln Arg Pro Tyr Cys Trp His Tyr Ala Pro Gln Pro Cys
            100                 105                 110

Gly Ile Val Pro Ala Leu Gln Val Cys Gly Pro Val Tyr Cys Phe Thr
        115                 120                 125

Pro Ser Pro Val Val Val Gly Thr Thr Asp Arg Phe Gly Val Pro Thr
    130                 135                 140

Tyr Asn Trp Gly Asp Asn Glu Thr Asp Val Leu Leu Leu Asn Asn Thr
145                 150                 155                 160

Arg Pro Pro Gln Gly Asn Trp Phe Gly Cys Thr Trp Met Asn Ser Thr
                165                 170                 175

Gly Phe Thr Lys Thr Cys Gly Gly Pro Pro Cys Asn Ile Gly Gly Ala
            180                 185                 190
```

-continued

```
Gly Asn Asn Thr Leu Thr Cys Pro Thr Asp Cys Phe Arg Lys His Pro
        195                 200                 205

Glu Ala Thr Tyr Thr Lys Cys Gly Ser Gly Pro Trp Leu Thr Pro Arg
    210                 215                 220

Cys Met Val Asp Tyr Pro Tyr Arg Leu Trp His Tyr Pro Cys Thr Phe
225                 230                 235                 240

Asn Phe Thr Ile Phe Lys Ile Arg Met Tyr Val Gly Gly Val Glu His
                245                 250                 255

Arg Leu Asn Ala Ala Cys Asn Trp Thr Arg Gly Glu Arg Cys Asn Ile
            260                 265                 270

Glu Asp Arg Asp Arg Ser Glu Leu Ser Pro Leu Leu Leu Ser Thr Thr
        275                 280                 285

Glu Trp Gln Ile Leu Pro Cys Ser Phe Thr Thr Leu Pro Ala Leu Ser
    290                 295                 300

Thr Gly Leu Ile His Leu His Gln Asn Ile Val Asp Val Gln Tyr Leu
305                 310                 315                 320

Tyr Gly Val Gly Ser Ala Val Val Ser Ile Val Ile Lys Trp Glu Tyr
                325                 330                 335

Val Leu Leu Leu Phe Leu Leu Leu Ala Asp Ala
            340                 345
```

<210> SEQ ID NO 10
<211> LENGTH: 1620
<212> TYPE: DNA
<213> ORGANISM: Artificial Sequence
<220> FEATURE:
<223> OTHER INFORMATION: Optimized sequence encoding HCV E1 + E2 proteins

<400> SEQUENCE: 10

```
atgtatgagg tgaggaatgt ctctggcgtc taccatgtga ccaatgactg ctccaactcc     60

tgcattgtct atgaggctgc tgacatgatc atgcacaccc ctggctgtgt gccatgtgtg    120

agggagggca actcctccag gtgctgggtg gccctgaccc ccaccctggc tgccaggaac    180

tcctccatcc ccaccaccac catcaggagg catgtggacc tgctggtggg cgctgctgcc    240

ctgtgctctg ccatgtatgt gggcgacctg tgtggctctg tcttcctggt gtcccagctg    300

ttcaccttct cccccaggag gtatgagact gtgcaggact gcaactgctc cctgtaccct    360

ggccatgtct ctggccacag gatggcctgg gacatgatga tgaactggtc ccccaccact    420

gccctggtgg tctcccagct gctgaggatc ccccaggctg tggtggacat ggtggtgggc    480

gcccactggg gcgtgctggc tggcctggcc tactactcca tggtgggcaa ctgggccaag    540

gtgctgattg tgatgctgct gtttgctggc gtggatggca ccacctatgt ctctgtgggc    600

catgcctccc agaccaccag gagggtggcc tccttcttct cccctggctc tgcccagaag    660

atccagctgg tgaacaccaa tggctcctgg cacatcaaca ggactgccct gaattgcaac    720

gagtccatca acactggctt ctttgctgcc ctgttctatg tgaagaagtt caactcctct    780

ggctgctctg agaggatggc ctcctgcagg cccattgaca ggtttgccca gggctggggc    840

cccatcaccc atgctgagtc caggtcctct gaccagaggc catactgctg gcactatgcc    900

ccccagccat gtggcattgt gcctgccctg caggtctgtg gccctgtcta ctgcttcacc    960

ccatcccctg tggtggtggg caccactgac aggtttggcg tgcccaccta caactggggc   1020

gacaatgaga ctgatgtgct gctgctgaac aacaccaggc ccccccaggg caactggttt   1080

ggctgcacct ggatgaactc cactggcttc accaagacct gtggcggccc cccatgcaac   1140
```

-continued

```
attggcggcg ctggcaacaa caccctgacc tgccccactg actgcttcag gaagcatcct  1200

gaggccacct acaccaagtg tggctctggc ccatggctga cccccaggtg catggtggac  1260

tacccataca ggctgtggca ctacccatgc accttcaact tcaccatctt caagatcagg  1320

atgtatgtgg gcggcgtgga gcacaggctg aatgctgcct gcaactggac caggggcgag  1380

aggtgcaaca ttgaggacag ggacaggtct gagctgtccc ccctgctgct gtccaccact  1440

gagtggcaga tcctgccatg ctccttcacc accctgcctg ccctgtccac tggcctgatc  1500

catctgcatc agaacattgt ggatgtgcag tacctgtacg gcgtgggctc cgctgtggtc  1560

tccattgtga tcaagtggga gtatgtgctg ctgctgttcc tgctgctggc tgatgcctaa  1620


<210> SEQ ID NO 11
<211> LENGTH: 539
<212> TYPE: PRT
<213> ORGANISM: Hepatitis C Virus

<400> SEQUENCE: 11

Met Tyr Glu Val Arg Asn Val Ser Gly Val Tyr His Val Thr Asn Asp
 1               5                  10                  15

Cys Ser Asn Ser Cys Ile Val Tyr Glu Ala Ala Asp Met Ile Met His
            20                  25                  30

Thr Pro Gly Cys Val Pro Cys Val Arg Glu Gly Asn Ser Ser Arg Cys
        35                  40                  45

Trp Val Ala Leu Thr Pro Thr Leu Ala Ala Arg Asn Ser Ser Ile Pro
    50                  55                  60

Thr Thr Thr Ile Arg Arg His Val Asp Leu Leu Val Gly Ala Ala Ala
65                  70                  75                  80

Leu Cys Ser Ala Met Tyr Val Gly Asp Leu Cys Gly Ser Val Phe Leu
                85                  90                  95

Val Ser Gln Leu Phe Thr Phe Ser Pro Arg Arg Tyr Glu Thr Val Gln
            100                 105                 110

Asp Cys Asn Cys Ser Leu Tyr Pro Gly His Val Ser Gly His Arg Met
        115                 120                 125

Ala Trp Asp Met Met Met Asn Trp Ser Pro Thr Thr Ala Leu Val Val
    130                 135                 140

Ser Gln Leu Leu Arg Ile Pro Gln Ala Val Val Asp Met Val Val Gly
145                 150                 155                 160

Ala His Trp Gly Val Leu Ala Gly Leu Ala Tyr Tyr Ser Met Val Gly
                165                 170                 175

Asn Trp Ala Lys Val Leu Ile Val Met Leu Leu Phe Ala Gly Val Asp
            180                 185                 190

Gly Thr Thr Tyr Val Ser Val Gly His Ala Ser Gln Thr Thr Arg Arg
        195                 200                 205

Val Ala Ser Phe Phe Ser Pro Gly Ser Ala Gln Lys Ile Gln Leu Val
    210                 215                 220

Asn Thr Asn Gly Ser Trp His Ile Asn Arg Thr Ala Leu Asn Cys Asn
225                 230                 235                 240

Glu Ser Ile Asn Thr Gly Phe Phe Ala Ala Leu Phe Tyr Val Lys Lys
                245                 250                 255

Phe Asn Ser Ser Gly Cys Ser Glu Arg Met Ala Ser Cys Arg Pro Ile
            260                 265                 270

Asp Arg Phe Ala Gln Gly Trp Gly Pro Ile Thr His Ala Glu Ser Arg
        275                 280                 285

Ser Ser Asp Gln Arg Pro Tyr Cys Trp His Tyr Ala Pro Gln Pro Cys
```

-continued

```
    290                 295                 300

Gly Ile Val Pro Ala Leu Gln Val Cys Gly Pro Val Tyr Cys Phe Thr
305                 310                 315                 320

Pro Ser Pro Val Val Val Gly Thr Thr Asp Arg Phe Gly Val Pro Thr
                325                 330                 335
Tyr Asn Trp Gly Asp Asn Glu Thr Asp Val Leu Leu Leu Asn Asn Thr
            340                 345                 350
Arg Pro Pro Gln Gly Asn Trp Phe Gly Cys Thr Trp Met Asn Ser Thr
        355                 360                 365
Gly Phe Thr Lys Thr Cys Gly Gly Pro Pro Cys Asn Ile Gly Gly Ala
    370                 375                 380

Gly Asn Asn Thr Leu Thr Cys Pro Thr Asp Cys Phe Arg Lys His Pro
385                 390                 395                 400

Glu Ala Thr Tyr Thr Lys Cys Gly Ser Gly Pro Trp Leu Thr Pro Arg
                405                 410                 415
Cys Met Val Asp Tyr Pro Tyr Arg Leu Trp His Tyr Pro Cys Thr Phe
            420                 425                 430

Asn Phe Thr Ile Phe Lys Ile Arg Met Tyr Val Gly Gly Val Glu His
        435                 440                 445

Arg Leu Asn Ala Ala Cys Asn Trp Thr Arg Gly Glu Arg Cys Asn Ile
    450                 455                 460

Glu Asp Arg Asp Arg Ser Glu Leu Ser Pro Leu Leu Leu Ser Thr Thr
465                 470                 475                 480

Glu Trp Gln Ile Leu Pro Cys Ser Phe Thr Thr Leu Pro Ala Leu Ser
                485                 490                 495

Thr Gly Leu Ile His Leu His Gln Asn Ile Val Asp Val Gln Tyr Leu
            500                 505                 510

Tyr Gly Val Gly Ser Ala Val Val Ser Ile Val Ile Lys Trp Glu Tyr
        515                 520                 525

Val Leu Leu Leu Phe Leu Leu Leu Ala Asp Ala
    530                 535


<210> SEQ ID NO 12
<211> LENGTH: 1350
<212> TYPE: DNA
<213> ORGANISM: Artificial Sequence
<220> FEATURE:
<223> OTHER INFORMATION: Optimized sequence encoding HCV NS5a protein

<400> SEQUENCE: 12

atgtctggct cctggctgag ggatgtctgg gactggatct gcactgtgct gactgacttc    60

aagacctggc tgcattccaa gctgctgccc aggctgcctg gcgacccatt cttctcctgc   120

cagaggggct acaggggcgt ctggaggggc gatggcgtga tgcagaccac ctgcccatgt   180

ggcgcccaga tcactggcca tgtgaagaat ggctccatga ggattgtggg ccccaagacc   240

tgctccaaca cctggcatgg caccttcccc atcaatgcct acaccactgg cccatgcacc   300

ccatcccctg cccccaacta ctccagggcc ctgtggaggg tggctgctga ggagtatgtg   360

gaggtgacca gggtgggcga cttccactat gtgactggca tgaccactga caatgtgaag   420

tgcccatgcc aggtgcctgc ccctgagttc ttcactgagg tggatggcgt gaggctgcac   480

aggtatgccc ctgcctgcaa gcccctgctg agggatgagg tgaccttcca ggtgggcctg   540

aaccagttcc ctgtgggctc ccagctgcca tgtgagcctg agcctgatgt gactgtgctg   600

acctccatgc tgactgagcc atcccacatc actgctgaga ctgccaagag gaggctggcc   660

aggggctccc ctccatccct ggcctcctcc tctgcctccc agctgtctgc tccatccctg   720

aaggccacct gcaccaccag gcatgactcc cctgatgctg acctgattga ggccaacctg   780
```

-continued

```
ctgtggaggc aggagatggg cggcaacatc accagggtgg agtctgagaa caaggtggtg   840

atcctggact cctttgagcc cctgagggct gaggaggatg agagggaggt ctctgtggct   900

gctgagatcc tgaggaagtc caggaagttc ccccctgccc tgcccatctg ggcgaggcca   960

tcctacaacc cacccctgct ggagtcctgg aaggaccctg actatgtgcc ccctgtggtg  1020

catggctgcc ccctgccccc caccatggcc ccacccatcc ccccacccag gaggaagagg  1080

actgtggtgc tgactgagtc cactgtctcc tctgccctgg ctgagctggc caccaagacc  1140

ttcggctcct ctggctcctc tgctgtggac tctggcactg ccacggcccc ccctgaccag  1200

ccatctgatg atggcgacag ggctctgat gatgagtcct actcctccat gccccccctg  1260

gagggcgagc ctggcgaccc tgacctgtct gatggctcct ggtccactgt ctctgaggag  1320

gcctctgagg atgtggcctg ctgctcctaa                                    1350


<210> SEQ ID NO 13
<211> LENGTH: 449
<212> TYPE: PRT
<213> ORGANISM: Hepatitis C Virus

<400> SEQUENCE: 13

Met Ser Gly Ser Trp Leu Arg Asp Val Trp Asp Trp Ile Cys Thr Val
 1               5                  10                  15

Leu Thr Asp Phe Lys Thr Trp Leu His Ser Lys Leu Leu Pro Arg Leu
            20                  25                  30

Pro Gly Asp Pro Phe Phe Ser Cys Gln Arg Gly Tyr Arg Gly Val Trp
        35                  40                  45

Arg Gly Asp Gly Val Met Gln Thr Thr Cys Pro Cys Gly Ala Gln Ile
    50                  55                  60

Thr Gly His Val Lys Asn Gly Ser Met Arg Ile Val Gly Pro Lys Thr
65                  70                  75                  80

Cys Ser Asn Thr Trp His Gly Thr Phe Pro Ile Asn Ala Tyr Thr Thr
                85                  90                  95

Gly Pro Cys Thr Pro Ser Pro Ala Pro Asn Tyr Ser Arg Ala Leu Trp
            100                 105                 110

Arg Val Ala Ala Glu Glu Tyr Val Glu Val Thr Arg Val Gly Asp Phe
        115                 120                 125

His Tyr Val Thr Gly Met Thr Thr Asp Asn Val Lys Cys Pro Cys Gln
    130                 135                 140

Val Pro Ala Pro Glu Phe Phe Thr Glu Val Asp Gly Val Arg Leu His
145                 150                 155                 160

Arg Tyr Ala Pro Ala Cys Lys Pro Leu Leu Arg Asp Glu Val Thr Phe
                165                 170                 175

Gln Val Gly Leu Asn Gln Phe Pro Val Gly Ser Gln Leu Pro Cys Glu
            180                 185                 190

Pro Glu Pro Asp Val Thr Val Leu Thr Ser Met Leu Thr Glu Pro Ser
        195                 200                 205

His Ile Thr Ala Glu Thr Ala Lys Arg Arg Leu Ala Arg Gly Ser Pro
    210                 215                 220

Pro Ser Leu Ala Ser Ser Ser Ala Ser Gln Leu Ser Ala Pro Ser Leu
225                 230                 235                 240

Lys Ala Thr Cys Thr Thr Arg His Asp Ser Pro Asp Ala Asp Leu Ile
                245                 250                 255

Glu Ala Asn Leu Leu Trp Arg Gln Glu Met Gly Gly Asn Ile Thr Arg
            260                 265                 270
```

-continued

```
Val Glu Ser Glu Asn Lys Val Val Ile Leu Asp Ser Phe Glu Pro Leu
        275                 280                 285

Arg Ala Glu Glu Asp Glu Arg Glu Val Ser Val Ala Ala Glu Ile Leu
    290                 295                 300

Arg Lys Ser Arg Lys Phe Pro Pro Ala Leu Pro Ile Trp Ala Arg Pro
305                 310                 315                 320

Ser Tyr Asn Pro Pro Leu Leu Glu Ser Trp Lys Asp Pro Asp Tyr Val
                325                 330                 335

Pro Pro Val Val His Gly Cys Pro Leu Pro Pro Thr Met Ala Pro Pro
            340                 345                 350

Ile Pro Pro Pro Arg Arg Lys Arg Thr Val Val Leu Thr Glu Ser Thr
        355                 360                 365

Val Ser Ser Ala Leu Ala Glu Leu Ala Thr Lys Thr Phe Gly Ser Ser
    370                 375                 380

Gly Ser Ser Ala Val Asp Ser Gly Thr Ala Thr Ala Pro Pro Asp Gln
385                 390                 395                 400

Pro Ser Asp Asp Gly Asp Arg Gly Ser Asp Asp Glu Ser Tyr Ser Ser
                405                 410                 415

Met Pro Pro Leu Glu Gly Glu Pro Gly Asp Pro Asp Leu Ser Asp Gly
            420                 425                 430

Ser Trp Ser Thr Val Ser Glu Glu Ala Ser Glu Asp Val Ala Cys Cys
        435                 440                 445

Ser


<210> SEQ ID NO 14
<211> LENGTH: 1773
<212> TYPE: DNA
<213> ORGANISM: Artificial Sequence
<220> FEATURE:
<223> OTHER INFORMATION: Optimized sequence encoding HCV NS5b protein

<400> SEQUENCE: 14

atgtcctaca cctggactgg cgccctgatc accccatgtg ctgctgagga gtccaagctg    60

cccatcaacc ccctgtccaa ctccctgctg aggcatcaca acatggtcta tgccaccacc   120

tccaggtctg ctggcctgag gcagaagaag gtgacctttg acaggctgca tgtgcctgat   180

gaccactaca gggatgtgct gaaggagatg aaggccaagg cctccactgt gaaggcgaag   240

ctgctgtctg tggaggaggc ctgcaagctg acccctcccc actctgccag gtccaagttt   300

ggctatggcg ccaaggatgt gaggaacctg tcctccaagg ctgtgaacca catccactct   360

gtctggaagg acctgctgga ggacactgag acccccattg acaccaccat catggccaag   420

aatgaggtct tctgtgtgca gcctgagaag ggcggcagga agcctgccag gctgattgtc   480

ttccctgagc tgggcgtgag ggtgtgtgag aagatggccc tgtatgatgt ggtctccacc   540

ctgccccagg ctgtgatggg ctcctcctat ggcttccagt actcccctgg ccagagggtg   600

gagttcctgg tgaatgcctg gaagtccaag aagaacccca tgggctttgc ctactgcacc   660

aggtgctttg actccactgt gactgagtct gacatcaggg tggaggagtc catctaccag   720

tgctgtgacc tggctcctga ggccaggcag gtgatcaggt ccctgactga gaggctgtac   780

attggcggcc ccctgaccaa ctccaagggc cagaactgtg gctacaggag gtgcagggcc   840

tctggcgtgc tgaccactaa ctgtggcaac accctgacct gctacctgaa ggcctctgct   900

gcttgcaggg ctgccaagct gcatgactgc accatgctgg tctgtggcga tgacctggtg   960

gtgatctgtg agtctgctgg cacccaggag gatgctgcct ccctgagggt cttcactgag  1020
```

-continued gccatgacca ggtactctgc ccccctggc gaccctcccc agcctgagta tgacctggag 1080
ctgatcacct cctgctcctc caatgtctct gtggcccatg atgcctctgg caagagggtc 1140
tactacctga ccagggaccc caccaccccc ctggccaggg ctgcctggga gactgccagg 1200
cacacccctg tgaactcctg gctgggcaac atcatcatgt atgcccccac cctgtgggcc 1260
aggatgatcc tgatgaccca cttcttctcc atcctgctgg cccaggagca gctggagaag 1320
gccctgggct gccagattta tggcgccacc tacttcattg agcccctgga cctgccccag 1380
atcatccaga ggctgcatgg cctgtctgcc ttctccctgc actcctactc ccctggcgag 1440
atcaacaggg tggcctcctg cctgaggaag ctgggcgtgc ccccctgag ggtgtggagg 1500 cacagggcca ggtctgtgag ggccaagctg ctgtcccagg gcggcagggc tgccacctgt 1560
ggcaagtacc tgttcaactg ggctgtgagg accaagctga agctgacccc catccctgct 1620
gcctcccagc tggacctgtc tggctggttt gtggctggct actctggcgg cgacatctac 1680
cactccctgt ccagggccag gcccaggtgg ttcatgtggt gcctgctgct gctgtctgtg 1740
ggcgtgggca tctacctgct gcccaacagg tga 1773

<210> SEQ ID NO 15
<211> LENGTH: 590
<212> TYPE: PRT
<213> ORGANISM: Hepatitis C Virus

<400> SEQUENCE: 15

Met Ser Tyr Thr Trp Thr Gly Ala Leu Ile Thr Pro Cys Ala Ala Glu
1 5 10 15

Glu Ser Lys Leu Pro Ile Asn Pro Leu Ser Asn Ser Leu Leu Arg His
20 25 30

His Asn Met Val Tyr Ala Thr Thr Ser Arg Ser Ala Gly Leu Arg Gln
35 40 45

Lys Lys Val Thr Phe Asp Arg Leu His Val Pro Asp Asp His Tyr Arg
50 55 60

Asp Val Leu Lys Glu Met Lys Ala Lys Ala Ser Thr Val Lys Ala Lys
65 70 75 80

Leu Leu Ser Val Glu Glu Ala Cys Lys Leu Thr Pro Pro His Ser Ala
85 90 95

Arg Ser Lys Phe Gly Tyr Gly Ala Lys Asp Val Arg Asn Leu Ser Ser
100 105 110

Lys Ala Val Asn His Ile His Ser Val Trp Lys Asp Leu Leu Glu Asp
115 120 125

Thr Glu Thr Pro Ile Asp Thr Thr Ile Met Ala Lys Asn Glu Val Phe
130 135 140

Cys Val Gln Pro Glu Lys Gly Gly Arg Lys Pro Ala Arg Leu Ile Val
145 150 155 160

Phe Pro Glu Leu Gly Val Arg Val Cys Glu Lys Met Ala Leu Tyr Asp
165 170 175

Val Val Ser Thr Leu Pro Gln Ala Val Met Gly Ser Ser Tyr Gly Phe
180 185 190

Gln Tyr Ser Pro Gly Gln Arg Val Glu Phe Leu Val Asn Ala Trp Lys
195 200 205

Ser Lys Lys Asn Pro Met Gly Phe Ala Tyr Cys Thr Arg Cys Phe Asp
210 215 220

Ser Thr Val Thr Glu Ser Asp Ile Arg Val Glu Glu Ser Ile Tyr Gln
225 230 235 240

-continued

Cys Cys Asp Leu Ala Pro Glu Ala Arg Gln Val Ile Arg Ser Leu Thr
245 250 255

Glu Arg Leu Tyr Ile Gly Gly Pro Leu Thr Asn Ser Lys Gly Gln Asn
260 265 270

Cys Gly Tyr Arg Arg Cys Arg Ala Ser Gly Val Leu Thr Thr Asn Cys
275 280 285

Gly Asn Thr Leu Thr Cys Tyr Leu Lys Ala Ser Ala Ala Cys Arg Ala
290 295 300

Ala Lys Leu His Asp Cys Thr Met Leu Val Cys Gly Asp Asp Leu Val
305 310 315 320

Val Ile Cys Glu Ser Ala Gly Thr Gln Glu Asp Ala Ala Ser Leu Arg
325 330 335

Val Phe Thr Glu Ala Met Thr Arg Tyr Ser Ala Pro Pro Gly Asp Pro
340 345 350

Pro Gln Pro Glu Tyr Asp Leu Glu Leu Ile Thr Ser Cys Ser Ser Asn
355 360 365

Val Ser Val Ala His Asp Ala Ser Gly Lys Arg Val Tyr Tyr Leu Thr
370 375 380

Arg Asp Pro Thr Thr Pro Leu Ala Arg Ala Ala Trp Glu Thr Ala Arg
385 390 395 400

His Thr Pro Val Asn Ser Trp Leu Gly Asn Ile Ile Met Tyr Ala Pro
405 410 415

Thr Leu Trp Ala Arg Met Ile Leu Met Thr His Phe Phe Ser Ile Leu
420 425 430

Leu Ala Gln Glu Gln Leu Glu Lys Ala Leu Gly Cys Gln Ile Tyr Gly
435 440 445

Ala Thr Tyr Phe Ile Glu Pro Leu Asp Leu Pro Gln Ile Ile Gln Arg
450 455 460

Leu His Gly Leu Ser Ala Phe Ser Leu His Ser Tyr Ser Pro Gly Glu
465 470 475 480

Ile Asn Arg Val Ala Ser Cys Leu Arg Lys Leu Gly Val Pro Pro Leu
485 490 495

Arg Val Trp Arg His Arg Ala Arg Ser Val Arg Ala Lys Leu Leu Ser
500 505 510

Gln Gly Gly Arg Ala Ala Thr Cys Gly Lys Tyr Leu Phe Asn Trp Ala
515 520 525

Val Arg Thr Lys Leu Lys Leu Thr Pro Ile Pro Ala Ala Ser Gln Leu
530 535 540

Asp Leu Ser Gly Trp Phe Val Ala Gly Tyr Ser Gly Gly Asp Ile Tyr
545 550 555 560

His Ser Leu Ser Arg Ala Arg Pro Arg Trp Phe Met Trp Cys Leu Leu
565 570 575

Leu Leu Ser Val Gly Val Gly Ile Tyr Leu Leu Pro Asn Arg
580 585 590

<210> SEQ ID NO 16
<211> LENGTH: 103
<212> TYPE: DNA
<213> ORGANISM: Artificial Sequence
<220> FEATURE:
<223> OTHER INFORMATION: Modified Vector Sequence

<400> SEQUENCE: 16
cttaagcgaa ggttactctt gtacctctgg tacttggtcg ggatggtgta gacggcgccg 60
aagtggacga agttcttcat ttgggccctt aagatttcag ctg 103

-continued

<210> SEQ ID NO 17
<211> LENGTH: 15
<212> TYPE: DNA
<213> ORGANISM: Artificial Sequence
<220> FEATURE:
<223> OTHER INFORMATION: Modified Vector Sequence

<400> SEQUENCE: 17
agatctacca tgagc 15

<210> SEQ ID NO 18
<211> LENGTH: 15
<212> TYPE: DNA
<213> ORGANISM: Artificial Sequence
<220> FEATURE:
<223> OTHER INFORMATION: Modified Vector Sequence

<400> SEQUENCE: 18
gccgaattcg cttcc 15

<210> SEQ ID NO 19
<211> LENGTH: 25
<212> TYPE: DNA
<213> ORGANISM: Artificial Sequence
<220> FEATURE:
<223> OTHER INFORMATION: Modified Vector Sequence

<400> SEQUENCE: 19
taaacccggg aattctaaag tcgac 25

<210> SEQ ID NO 20
<211> LENGTH: 12
<212> TYPE: DNA
<213> ORGANISM: Artificial Sequence
<220> FEATURE:
<223> OTHER INFORMATION: Modified Vector Sequence

<400> SEQUENCE: 20
atcaccatgg at 12

<210> SEQ ID NO 21
<211> LENGTH: 15
<212> TYPE: DNA
<213> ORGANISM: Artificial Sequence
<220> FEATURE:
<223> OTHER INFORMATION: Modified Vector Sequence

<400> SEQUENCE: 21
gagatcttca tgagc 15

<210> SEQ ID NO 22
<211> LENGTH: 15
<212> TYPE: DNA
<213> ORGANISM: Artificial Sequence
<220> FEATURE:
<223> OTHER INFORMATION: Modified Vector Sequence

<400> SEQUENCE: 22
agatccacca tgcag 15

<210> SEQ ID NO 23
<211> LENGTH: 18
<212> TYPE: DNA
<213> ORGANISM: Artificial Sequence
<220> FEATURE:

-continued

<223> OTHER INFORMATION: Modified Vector Sequence

<400> SEQUENCE: 23
ggtgcagatc tgatgagc 18

<210> SEQ ID NO 24
<211> LENGTH: 13
<212> TYPE: DNA
<213> ORGANISM: Artificial Sequence
<220> FEATURE:
<223> OTHER INFORMATION: Modified Vector Sequence

<400> SEQUENCE: 24
gcctaaagtc gac 13

<210> SEQ ID NO 25
<211> LENGTH: 4261
<212> TYPE: DNA
<213> ORGANISM: Artificial Sequence
<220> FEATURE:
<223> OTHER INFORMATION: Modified Vector Sequence

<400> SEQUENCE: 25
gatattggct attggccatt gcatacgttg tatccatatc ataatatgta catttatatt 60
ggctcatgtc caacattacc gccatgttga cattgattat tgactagtta ttaatagtaa 120
tcaattacgg ggtcattagt tcatagccca tatatggagt tccgcgttac ataacttacg 180
gtaaatggcc cgcctggctg accgcccaac gacccccgcc cattgacgtc aataatgacg 240
tatgttccca tagtaacgcc aatagggact ttccattgac gtcaatgggt ggagtattta 300
cggtaaactg cccacttggc agtacatcaa gtgtatcata tgccaagtac gccccctatt 360
gacgtcaatg acggtaaatg gcccgcctgg cattatgccc agtacatgac cttatgggac 420
tttcctactt ggcagtacat ctacgtatta gtcatcgcta ttaccatggt gatgcggttt 480
tggcagtaca tcaatgggcg tggatagcgg tttgactcac ggggatttcc aagtctccac 540
cccattgacg tcaatgggag tttgttttgg caccaaaatc aacgggactt tccaaaatgt 600
cgtaacaact ccgccccatt gacgcaaatg ggcggtaggc gtgtacggtg ggaggtctat 660
ataagcagag ctcgtttagt gaaccgtcag atcgcctgga gacgccatcc acgctgtttt 720
gacctccata gaagacaccg ggaccgatcc agcctccgcg gccgggaacg gtgcattgga 780
acgcggattc cccgtgccaa gagtgacgta agtaccgcct atagagtcta taggcccacc 840
cccttggctt cttatgcatg ctatactgtt tttggcttgg ggtctataca cccccgcttc 900
ctcatgttat aggtgatggt atagcttagc ctataggtgt gggttattga ccattattga 960
ccactcccct attggtgacg atactttcca ttactaatcc ataacatggc tctttgccac 1020
aactctcttt attggctata tgccaataca ctgtccttca gagactgaca cggactctgt 1080
atttttacag gatggggtct catttattat ttacaaattc acatatacaa caccaccgtc 1140
cccagtgccc gcagttttta ttaaacataa cgtgggatct ccacgcgaat ctcgggtacg 1200
tgttccggac atgggctctt ctccggtagc ggcggagctt ctacatccga gccctgctcc 1260
catgcctcca gcgactcatg gtcgctcggc agctccttgc tcctaacagt ggaggccaga 1320
cttaggcaca gcacgatgcc caccaccacc agtgtgccgc acaaggccgt ggcggtaggg 1380
tatgtgtctg aaaatgagct cggggagcgg gcttgcaccg ctgacgcatt tggaagactt 1440
aaggcagcgg cagaagaaga tgcaggcagc tgagttgttg tgttctgata agagtcagag 1500
gtaactcccg ttgcggtgct gttaacggtg gagggcagtg tagtctgagc agtactcgtt 1560

-continued

```
gctgccgcgc gcgccaccag acataatagc tgacagacta acagactgtt cctttccatg  1620
ggtcttttct gcagtcaccg tccttagatc taccatgagc accaacccca agccccagag  1680
gaagaccaag aggaacacca acaggaggcc ccaggatgtg aagttccctg ggggaggcca  1740
gattgtggga ggggtctacc tgctgcccag gaggggcccc aggctggggg tgagggctac  1800
caggaagacc tctgagaggt cccagcccag gggcaggagg cagcccatcc ccaaggccag  1860
gaggcctgag ggccgctcct gggcccagcc tggctacccc tggcccctgt atggcaatga  1920
aggctttggc tgggctggct ggctgctgtc cccccagggc tccaggccct cctggggccc  1980
cacagacccc aggaggaggt ccaggaacct gggcaaggtg attgacaccc tgacctgtgg  2040
ctttgctgac ctgatgggct acatcccccct ggtgggggct cctgtgggag gggtggctag  2100
ggctctggct catggggtga gggtgctgga ggatggggtg aactatgcta ctggcaacct  2160
gcctggctgc tccttctcca tcttcctgct ggccctgctc tcctgcctga cagtgcctgc  2220
ttctgccgaa ttcgcttcca atgagaacat ggagaccatg aaccagccct accacatctg  2280
ccgcggcttc acctgcttca agaagtaaac ccgggaattc taaagtcgac agcggccgcg  2340
atctgctgtg ccttctagtt gccagccatc tgttgtttgc ccctcccccg tgccttcctt  2400
gaccctggaa ggtgccactc ccactgtcct ttcctaataa aatgaggaaa ttgcatcgca  2460
ttgtctgagt aggtgtcatt ctattctggg gggtggggtg gggcagcaca gcaaggggga  2520
ggattgggaa gacaatagca ggcatgctgg ggatgcggtg ggctctatgg gtacggccgc  2580
agcggcctta attaaggccg cagcggccgt acccaggtgc tgaagaattg acccggttcc  2640
tcgacccgta aaaaggccgc gttgctggcg tttttccata ggctccgccc ccctgacgag  2700
catcacaaaa atcgacgctc aagtcagagg tggcgaaacc cgacaggact ataaagatac  2760
caggcgtttc cccctggaag ctccctcgtg cgctctcctg ttccgaccct gccgcttacc  2820
ggatacctgt ccgcctttct cccttcggga agcgtggcgc tttctcaatg ctcacgctgt  2880
aggtatctca gttcggtgta ggtcgttcgc tccaagctgg gctgtgtgca cgaacccccc  2940
gttcagcccg accgctgcgc cttatccggt aactatcgtc ttgagtccaa cccggtaaga  3000
cacgacttat cgccactggc agcagccact ggtaacagga ttagcagagc gaggtatgta  3060
ggcggtgcta cagagttctt gaagtggtgg cctaactacg gctacactag aaggacagta  3120
tttggtatct gcgctctgct gaagccagtt accttcggaa aaagagttgg tagctcttga  3180
tccggcaaac aaaccaccgc tggtagcggt ggtttttttg tttgcaagca gcagattacg  3240
cgcagaaaaa aaggatctca agaagatcct ttgatctttt ctacgtgatc ccgtaatgct  3300
ctgccagtgt tacaaccaat taaccaattc tgattagaaa aactcatcga gcatcaaatg  3360
aaactgcaat ttattcatat caggattatc aataccatat ttttgaaaaa gccgtttctg  3420
taatgaagga gaaaactcac cgaggcagtt ccataggatg gcaagatcct ggtatcggtc  3480
tgcgattccg actcgtccaa catcaataca acctattaat ttcccctcgt caaaaataag  3540
gttatcaagt gagaaatcac catgagtgac gactgaatcc ggtgagaatg gcaaaagctt  3600
atgcatttct ttccagactt gttcaacagg ccagccatta cgctcgtcat caaaatcact  3660
cgcatcaacc aaaccgttat tcattcgtga ttgcgcctga gcgagacgaa atacgcgatc  3720
gctgttaaaa ggacaattac aaacaggaat cgaatgcaac cggcgcagga acactgccag  3780
cgcatcaaca atattttcac ctgaatcagg atattcttct aatacctgga atgctgtttt  3840
cccggggatc gcagtggtga gtaaccatgc atcatcagga gtacggataa aatgcttgat  3900
```

-continued

| | |
|---|---|
| ggtcggaaga ggcataaatt ccgtcagcca gtttagtctg accatctcat ctgtaacatc | 3960 |
| attggcaacg ctacctttgc catgtttcag aaacaactct ggcgcatcgg gcttcccata | 4020 |
| caatcgatag attgtcgcac ctgattgccc gacattatcg cgagcccatt tatacccata | 4080 |
| taaatcagca tccatgttgg aatttaatcg cggcctcgag caagacgttt cccgttgaat | 4140 |
| atggctcata acaccccttg tattactgtt tatgtaagca gacagtttta ttgttcatga | 4200 |
| tgatatattt ttatcttgtg caatgtaaca tcagagattt tgagacacaa cgtggctttc | 4260 |
| c | 4261 |

What is claimed is:

1. A polynucleotide comprising the nucleotide sequence of SEQ ID NO: 2.

2. The polynucleotide of claim 1, wherein said polynucleotide is a plasmid vector that expresses said nucleotide sequence in a vertebrate host such that said nucleotide sequence is translated into a polypeptide.

3. The polynucleotide of claim 1, wherein said polynucleotide consists of the nucleotide sequence of SEQ ID NO: 25.

* * * * *